(12) United States Patent
Ginn et al.

(10) Patent No.: US 11,147,675 B2
(45) Date of Patent: Oct. 19, 2021

(54) SYSTEM FOR SACRO-ILIAC STABILIZATION

(71) Applicant: Tenon Medical, Inc., Palo Alto, CA (US)

(72) Inventors: Richard S. Ginn, Gilroy, CA (US); Scott Yerby, Montara, CA (US); Nicanor Domingo, Santa Clara, CA (US); Hans F. Valencia, San Jose, CA (US); Robert Elliot DeCou, San Carlos, CA (US)

(73) Assignee: Tenon Medical, Inc., Los Gatos, CA (US)

( * ) Notice: Subject to any disclaimer, the term of this patent is extended or adjusted under 35 U.S.C. 154(b) by 0 days.

(21) Appl. No.: 15/349,632

(22) Filed: Nov. 11, 2016

(65) Prior Publication Data
US 2017/0245999 A1 Aug. 31, 2017

Related U.S. Application Data

(63) Continuation of application No. 13/857,978, filed on Apr. 5, 2013, now Pat. No. 9,492,284, which is a
(Continued)

(51) Int. Cl.
*A61F 2/44* (2006.01)
*A61B 17/70* (2006.01)
(Continued)

(52) U.S. Cl.
CPC .......... *A61F 2/30988* (2013.01); *A61B 5/055* (2013.01); *A61B 5/062* (2013.01);
(Continued)

(58) Field of Classification Search
CPC ................ A61B 17/16; A61B 17/1637; A61B 17/32002; A61F 2/30988;
(Continued)

(56) References Cited

U.S. PATENT DOCUMENTS 2,818,854 A 1/1958 Willard
4,545,374 A 10/1985 Jacobson
(Continued)

FOREIGN PATENT DOCUMENTS

WO 2008/088685 7/2008
WO 2010/045749 A1 4/2010
(Continued)

OTHER PUBLICATIONS

International Preliminary Report on Patentability and Written Opinion dated Jan. 29, 2013 for International Patent Appln. No. PCT/US2011/045615 filed Jul. 27, 2011.
(Continued)

*Primary Examiner* — Eduardo C Robert
*Assistant Examiner* — Tara Rose E Carter
(74) *Attorney, Agent, or Firm* — Francis Law Group

(57) ABSTRACT

Configurations are described for conducting minimally invasive medical interventions utilizing elongate instruments and assemblies thereof to stabilize and/or fixate a sacro-iliac joint. In one embodiment, a tool assembly may be advanced from a posterior approach into the SI junction and configured to create a defect defined at least in part by portions of both the sacrum and the ilium, the defect having a three dimensional shape defined in part by at least one noncircular cross sectional shape in a plane substantially perpendicular to the longitudinal axis of the tool assembly. After a defect is created, the tool assembly may be retracted and a prosthesis deployed into the defect.

7 Claims, 47 Drawing Sheets

Related U.S. Application Data continuation of application No. 13/192,289, filed on Jul. 27, 2011, now abandoned.

(60) Provisional application No. 61/368,233, filed on Jul. 27, 2010.

(51) Int. Cl.
| | | |
|---|---|---|
| *A61B 17/88* | (2006.01) | |
| *A61F 2/46* | (2006.01) | |
| *A61F 2/30* | (2006.01) | |
| *A61B 17/16* | (2006.01) | |
| *A61B 5/055* | (2006.01) | |
| *A61B 5/06* | (2006.01) | |
| *A61B 6/03* | (2006.01) | |
| *A61B 6/00* | (2006.01) | |
| *A61B 8/08* | (2006.01) | |
| *A61B 34/20* | (2016.01) | |

(52) U.S. Cl.
CPC .............. *A61B 6/032* (2013.01); *A61B 6/485* (2013.01); *A61B 8/0841* (2013.01); *A61B 17/1604* (2013.01); *A61B 17/1664* (2013.01); *A61B 17/1671* (2013.01); *A61B 17/70* (2013.01); *A61B 17/7055* (2013.01); *A61B 17/7074* (2013.01); *A61B 17/8858* (2013.01); *A61B 34/20* (2016.02); *A61F 2/4455* (2013.01); *A61F 2/4601* (2013.01); *A61F 2/4611* (2013.01); *A61B 2576/00* (2013.01); *A61F 2002/30121* (2013.01); *A61F 2002/30123* (2013.01); *A61F 2002/30166* (2013.01); *A61F 2002/30593* (2013.01); *A61F 2002/30995* (2013.01)

(58) Field of Classification Search
CPC .. A61F 2002/30166; A61F 2002/30593; A61F 2002/30995; A61F 2002/30121; A61F 2002/30123
USPC ................ 606/79–86 R; 623/17.11–17.16
See application file for complete search history.

(56) References Cited

U.S. PATENT DOCUMENTS

| | | |
|---|---|---|
| 4,662,891 A | 5/1987 | Noiles |
| 4,787,378 A | 11/1988 | Sodhi |
| 4,961,740 A | 10/1990 | Ray et al. |
| 5,108,397 A | 4/1992 | White |
| 5,334,205 A | 8/1994 | Cain |
| 5,445,639 A | 8/1995 | Kuslich et al. |
| 5,484,437 A | 1/1996 | Michelson |
| 5,928,239 A | 7/1999 | Mirza |
| 6,053,916 A | 4/2000 | Moore |
| 6,444,693 B1 | 9/2002 | Wachendorff-Neumann et al. |
| 6,470,004 B1 | 10/2002 | Murata |
| 7,914,530 B2 | 3/2011 | Michelson |
| 7,922,765 B2 | 4/2011 | Reiley |
| 8,162,981 B2 | 4/2012 | Vestgaarden |
| 8,221,428 B2 | 7/2012 | Tried |
| 8,343,189 B2 | 1/2013 | Assell et al. |
| 8,348,950 B2 | 1/2013 | Assell et al. |
| 8,388,667 B2 | 3/2013 | Reiley |
| 8,414,648 B2 | 4/2013 | Reiley |
| 8,419,722 B2 | 4/2013 | Richards et al. |
| 8,425,570 B2 | 4/2013 | Reiley |
| 8,551,171 B2 | 10/2013 | Johnson et al. |
| 8,623,053 B2 | 1/2014 | Vestgaarden |
| 9,492,284 B2* | 11/2016 | Ginn .................. A61B 17/1604 |
| 2003/0032098 A1 | 2/2003 | Voung et al. |
| 2004/0267269 A1 | 12/2004 | Middleton et al. |
| 2006/0036322 A1* | 2/2006 | Reiley .................. A61F 2/4455 623/17.11 |
| 2006/0054171 A1 | 3/2006 | Dall |
| 2006/0089646 A1 | 4/2006 | Bonutti |
| 2007/0118224 A1* | 5/2007 | Shah .................. A61B 17/1757 623/17.15 |
| 2007/0156241 A1* | 7/2007 | Reiley ................ A61B 17/1615 623/17.11 |
| 2007/0270879 A1 | 11/2007 | Isaza et al. |
| 2008/0009861 A1* | 1/2008 | Stark ...................... A61B 17/68 606/914 |
| 2008/0039843 A1 | 2/2008 | Abdou |
| 2008/0140082 A1 | 6/2008 | Erdem et al. |
| 2009/0099610 A1* | 4/2009 | Johnson ............... A61B 17/844 606/86 R |
| 2009/0138015 A1 | 5/2009 | Conner et al. |
| 2009/0216238 A1 | 8/2009 | Stark |
| 2009/0259261 A1 | 10/2009 | Reiley |
| 2010/0106200 A1 | 4/2010 | Stark |
| 2010/0268228 A1* | 10/2010 | Petersen ............. A61F 2/30988 606/60 |
| 2011/0087294 A1 | 4/2011 | Reiley |
| 2011/0098709 A1 | 4/2011 | Malandain et al. |
| 2011/0125268 A1 | 5/2011 | Reiley |
| 2011/0184518 A1 | 7/2011 | Trieu |
| 2011/0184520 A1 | 7/2011 | Trieu |
| 2011/0230966 A1 | 9/2011 | Trieu |
| 2011/0238181 A1 | 9/2011 | Trieu |
| 2011/0264229 A1* | 10/2011 | Donner ............... A61F 2/30988 623/18.11 |
| 2011/0295272 A1 | 12/2011 | Assell et al. |
| 2011/0301407 A1 | 12/2011 | Deitch |
| 2012/0022535 A1 | 1/2012 | Mayer et al. |
| 2012/0083883 A1 | 4/2012 | Ginn |
| 2012/0095560 A1 | 4/2012 | Donner |
| 2012/0191191 A1 | 7/2012 | Trieu |
| 2012/0296428 A1 | 11/2012 | Donner |
| 2013/0030456 A1 | 1/2013 | Assell et al. |
| 2013/0035723 A1 | 2/2013 | Donner et al. |
| 2013/0053902 A1 | 2/2013 | Trudeau |
| 2013/0085535 A1 | 4/2013 | Greenhalgh et al. |
| 2013/0144343 A1 | 6/2013 | Arnett et al. |
| 2013/0172736 A1 | 7/2013 | Abdou |
| 2013/0184769 A1 | 7/2013 | Reiley |
| 2013/0197590 A1 | 8/2013 | Assell et al. |
| 2013/0226301 A1 | 8/2013 | Reiley |
| 2013/0237988 A1 | 9/2013 | Mauldin |
| 2013/0238031 A1 | 9/2013 | Reiley |
| 2013/0238093 A1 | 9/2013 | Mauldin et al. |
| 2013/0245764 A1 | 9/2013 | Mauldin |
| 2013/0253654 A1 | 9/2013 | Reiley |
| 2013/0267836 A1 | 10/2013 | Mauldin et al. |
| 2013/0267961 A1 | 10/2013 | Mauldin et al. |
| 2013/0267989 A1 | 10/2013 | Mauldin et al. |
| 2013/0282012 A1 | 10/2013 | Stark |
| 2013/0289625 A1 | 10/2013 | Reiley |
| 2013/0296953 A1 | 11/2013 | Mauldin et al. |
| 2014/0135927 A1 | 5/2014 | Pavlov et al. |

FOREIGN PATENT DOCUMENTS

| | | |
|---|---|---|
| WO | 2010/065015 | 6/2010 |
| WO | 2011/087912 A1 | 7/2011 |

OTHER PUBLICATIONS

EP Examination Report dated Apr. 25, 2016 for European Appln. No. 11749987.1, 7 pages.

EP Decision of the Examining Division dated Sep. 27, 2017 for European Appln. No. 11749987.1, 13 pages.

\* cited by examiner

SYSTEM FOR SACRO-ILIAC STABILIZATION

CROSS-REFERENCE TO RELATED APPLICATIONS

This application is a continuation application of U.S. patent application Ser. No. 13/857,978 filed Apr. 5, 2013, which is a continuation application of U.S. patent application Ser. No. 13/192,289 filed Jul. 27, 2011, now abandoned, which claims the benefit of U.S. provisional patent application Ser. No. 61/368,233 filed Jul. 27, 2010. The foregoing applications are hereby incorporated by reference into the present application in their entirety. Priority to the aforementioned applications is hereby expressly claimed in accordance with 35 U.S.C. §§ 119, 120, 365 and 371 and any other applicable statutes.

FIELD OF THE INVENTION

The present invention relates generally to stabilization and/or fixation of adjacent bony structures of the skeletal system, and more particularly to a minimally invasive system and method for stabilizing and/or fixating the sacro-iliac joint of the human.

BACKGROUND

Back pain may be decreased or eliminated through stabilization or fusion of certain skeletal joints of the body, such as the sacro-iliac ("SI") joint of the spine. Referring to FIG. 1A, the SI joint (6) is located at the juncture of the ilium (4), the upper bone of the pelvis, and the sacrum (2) at the base of the spine. While the sacroiliac joint (6) has a limited range of motion, dysfunction of the joint has been identified and associated with fairly significant negative impacts upon normal activity in some cases. Important soft tissue structures, such as ligaments, vessels, and nerves surround the SI joint, making intervention challenging. It would be valuable to have a means for minimally invasively stabilizing and/or fixating the SI joint in patients requiring such intervention, from an approach that does not compromise the important surrounding soft tissue structures.

SUMMARY

One embodiment is directed to a method of stabilizing an SI joint, comprising advancing a tool assembly from a posterior approach into an SI junction defined between sacrum and ilium structures of a patient, the tool assembly being configured to create a defect defined at least in part by portions of both the sacrum and the ilium, the defect having a three dimensional shape defined in part by at least one noncircular cross sectional shape in a plane substantially perpendicular to the longitudinal axis of the tool assembly; creating a defect with the tool assembly; retracting the tool assembly; and deploying a prosthesis into the defect. The method may further comprise advancing an elongate guiding member into the SI junction, confirming a position of the guiding member in the SI junction, and using the guiding member as a mechanical guide while advancing the tool assembly into the SI junction. Confirming may comprise intraoperatively capturing images of the guiding member relative to portions of the sacrum and ilium. The images may be captured with a modality selected from the group consisting of fluoroscopy, CT, ultrasound, radiography, and magnetic resonance imaging. Creating a defect may comprise mechanically actuating at least a portion the tool assembly, such as by inducing insertion/retraction or rotational motion to a portion of the tool assembly. Advancing a tool assembly from a posterior approach may comprise manually inserting. Advancing a tool assembly from a posterior approach may comprise urging the tool assembly forward using a tool selected from the group consisting of a hammer, a drill, a solenoid, and a piston. Advancing a tool assembly from a posterior approach may comprise dislodging one or more portions of the sacrum, ilium, or both. The tool assembly may comprise one or more coring devices configured to dislodge and remove one or more portions of the sacrum, ilium, or both. At least one noncircular cross sectional shape may be selected from the group consisting of: an oval shape, an elliptical shape, a multilobed shape, an "H" shape, an "arcuate-H" shape, a rectangular shape, and a square shape. The at least one noncircular cross sectional shape may further comprise one or more leg portions extending away from the noncircular cross sectional shape. One or more of the leg portions may comprise a shape selected from the group consisting of a straight leg, an arcuate leg, and a multisegmented leg. The method may further comprise inserting into at least a portion of the prosthesis a material selected from the group consisting of: demineralized bone matrix, autograft bone material, allograft bone material, polymethylmethacrylate, calcium-based bone void filler material, and bone morphogenic protein, such as one selected from the group consisting of BMP-1, BMP-7, and OP-1. The tool assembly may be configured to create a defect shape which varies in cross section relative to the longitudinal axis of the tool assembly. The tool assembly may be configured to create a defect having a proximal cross sectional shape which is greater in area that a corresponding distal cross sectional shape.

Another embodiment is directed to a system for stabilizing an SI joint, comprising a defect-creating tool assembly configured to be advanced from a posterior approach into an SI junction defined between sacrum and ilium structures of a patient, the tool assembly being configured to create a defect defined at least in part by portions of both the sacrum and the ilium, the defect having a three dimensional shape defined in part by at least one noncircular cross sectional shape in a plane substantially perpendicular to the longitudinal axis of the tool assembly; and a prosthesis configured to fit into the defect created by the tool assembly. The tool assembly may comprise one or more coring devices configured to dislodge and remove one or more portions of the sacrum, ilium, or both. The system may further comprise a tool assembly advancing device selected from the group consisting of a hammer, a drill, a solenoid, and a piston. The system may further comprise an image capture device configured to intraoperatively capture images of the tool assembly relative to portions of the sacrum and ilium. The image capture device may be selected from the group consisting of a fluoroscope, a CT system, an ultrasound system, a radiography system, and a magnetic resonance imaging system. The system may further comprise a fixation catalyst configured to fit into the defect along with the prosthesis, the catalyst selected from the group consisting of: demineralized bone matrix, autograft bone material, allograft bone material, polymethylmethacrylate, calcium-based bone void filler material, and bone morphogenic protein, such as one selected from the group consisting of BMP-1, BMP-7, and OP-1. The at least one noncircular cross sectional shape may be selected from the group consisting of: an oval shape, an elliptical shape, a multilobed shape, an "H" shape, an "arcuate-H" shape, a rectangular shape, and a square shape. The at least one noncircular cross sectional shape may further comprise one or more leg portions extending away from the noncircular cross sectional shape. One or more of the leg portions may comprise a shape selected from the group consisting of a straight leg, an arcuate leg, and a multisegmented leg. The tool assembly may be configured to create a defect shape which varies in cross section relative to the longitudinal axis of the tool assembly. The tool assembly may be configured to create a defect having a proximal cross sectional shape which is greater in area that a corresponding distal cross sectional shape.

DETAILED DESCRIPTION

Figure 1A:
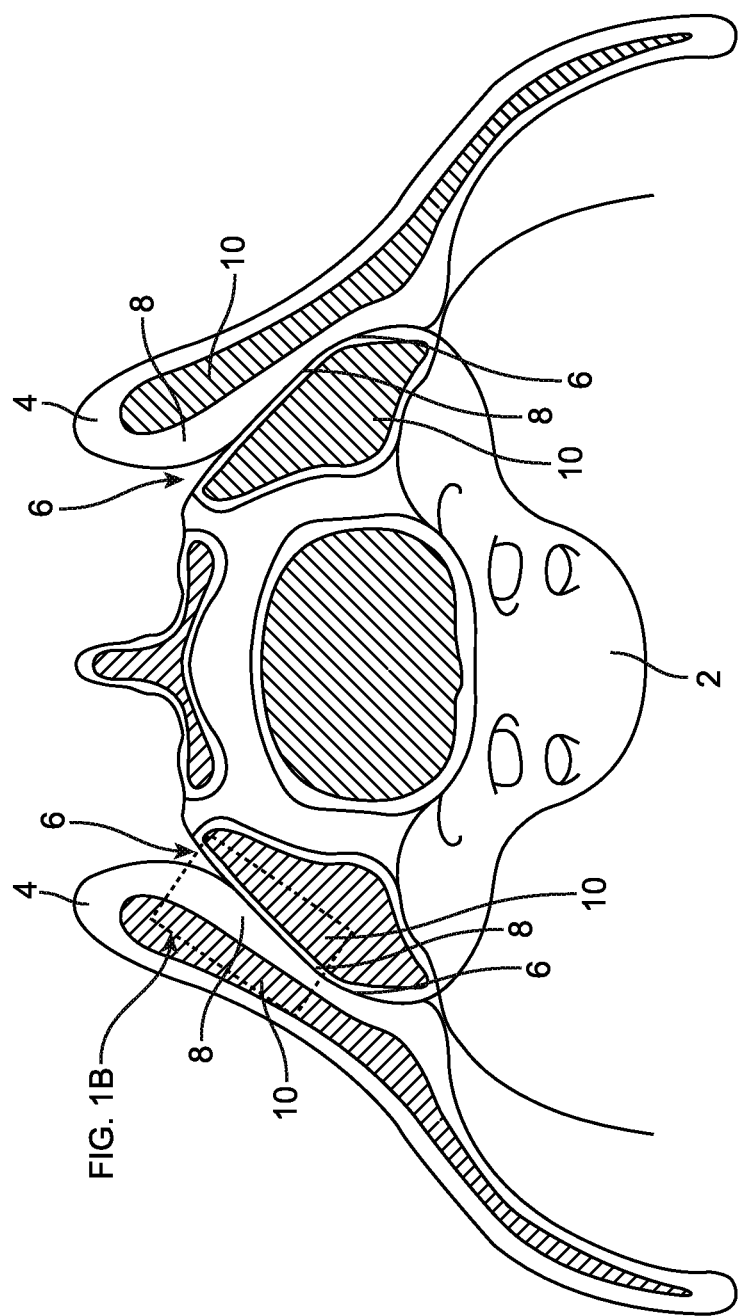
FIGS. 1A-1C illustrate aspects of sacro-iliac anatomy.
Figure 1B:
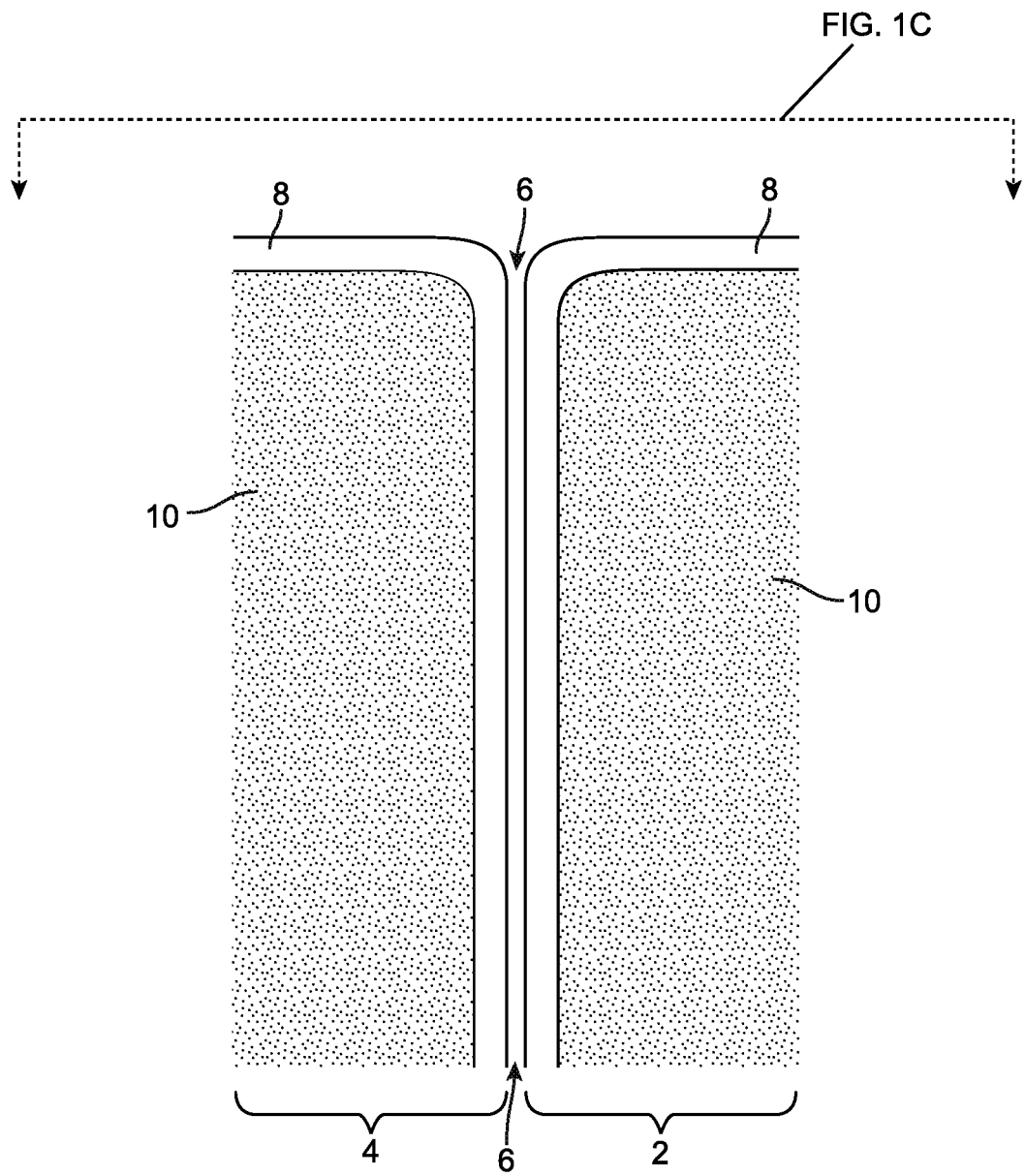
Figure 1C:
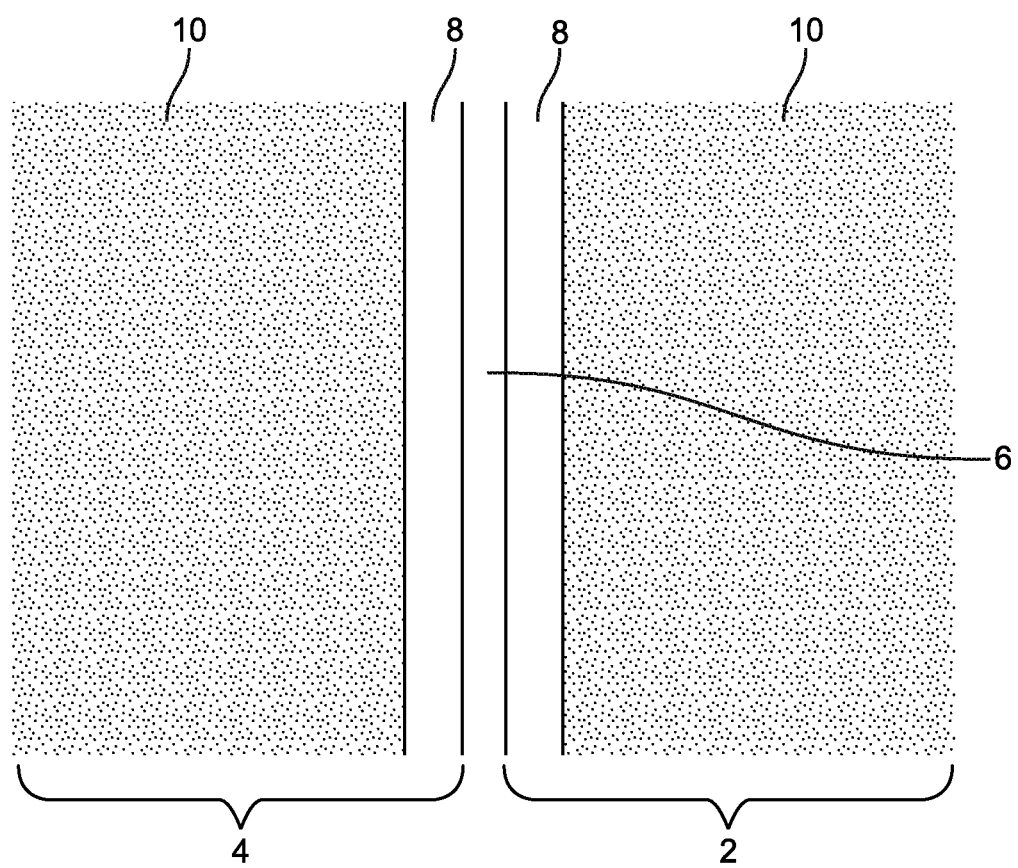
Figure 2:
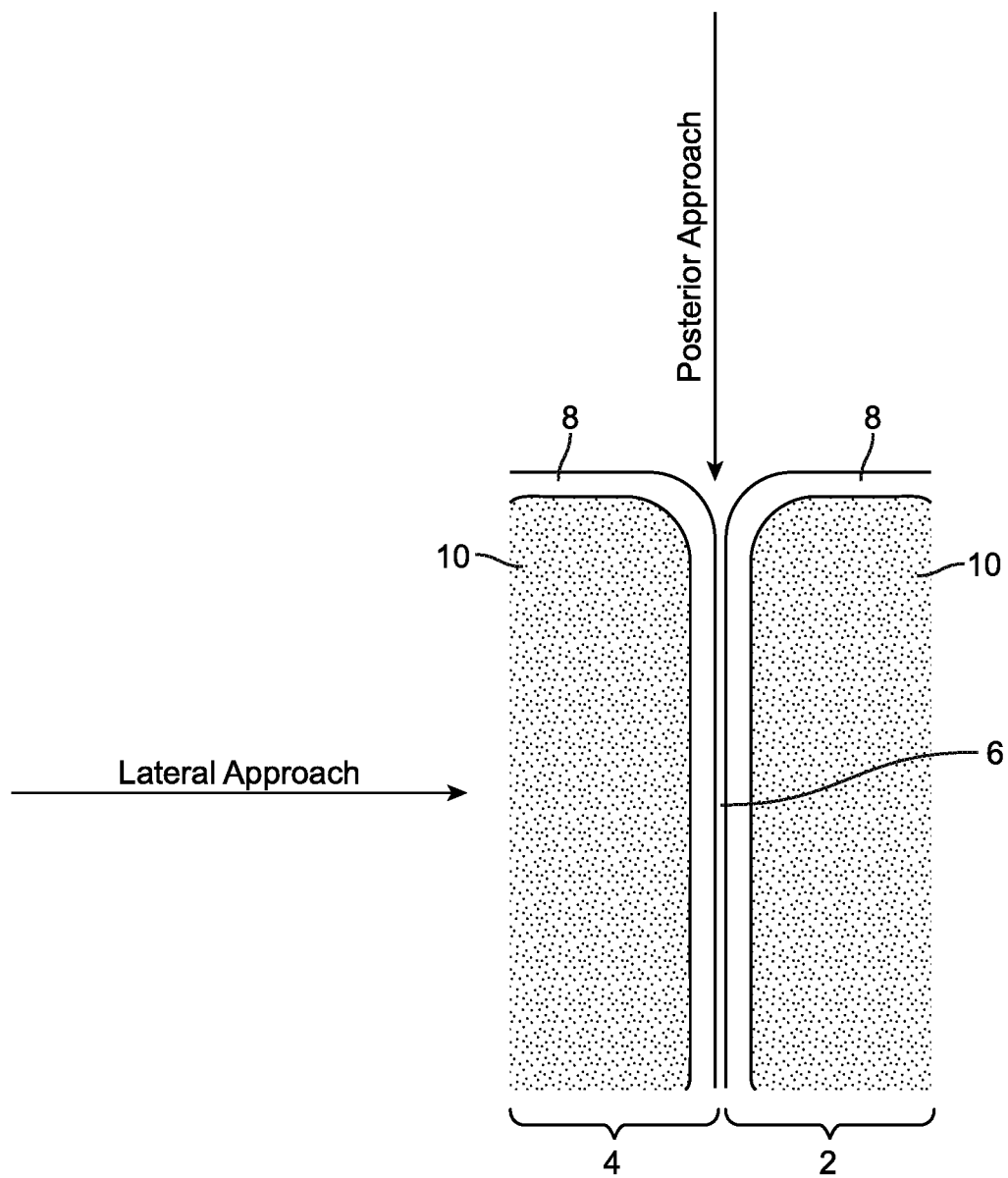
FIG. 2 illustrates two approaches to the sacro-iliac joint.

Referring again to FIG. 1A, the SI joint (6) is defined by the interface between articulating surfaces of the sacrum (2) and the ilium (4). Each of these bony structures comprises a combination of trabecular bone (10) and cortical bone (8), and generally the surfaces of the bones most adjacent the SI joint (6) comprise cortical bone (8), which is more compact, dense, and hard relative to trabecular bone (10), which generally is located at interior regions of bony structures. FIG. 1B depicts a close up illustration of a portion of the leftmost SI joint (6) illustrated in FIG. 1A. For illustrative simplicity, a uniform layer of cortical bone (8) is shown adjacent a deeper layer of trabecular bone (10) on both of the depicted sacrum (2) and ilium (4) portions; in live anatomy, such layers are far less uniform and homogeneous. FIG. 1C illustrates a view of the same structure from a different orthogonal perspective. From the perspective of FIG. 1C, a posterior approach to the SI joint (6) would be substantially perpendicular to the page upon which FIG. 1C is printed. Indeed, referring to FIG. 2, a variation similar to that depicted in FIG. 1B is illustrated, showing an approximate approach vector for a lateral approach to the SI joint (6) versus a posterior approach, using the orientation paradigms introduced in FIGS. 1A-1C. Such paradigm is used to illustrate various embodiments of the subject invention in various figures that follow FIGS. 1A-2.

Figure 3A:
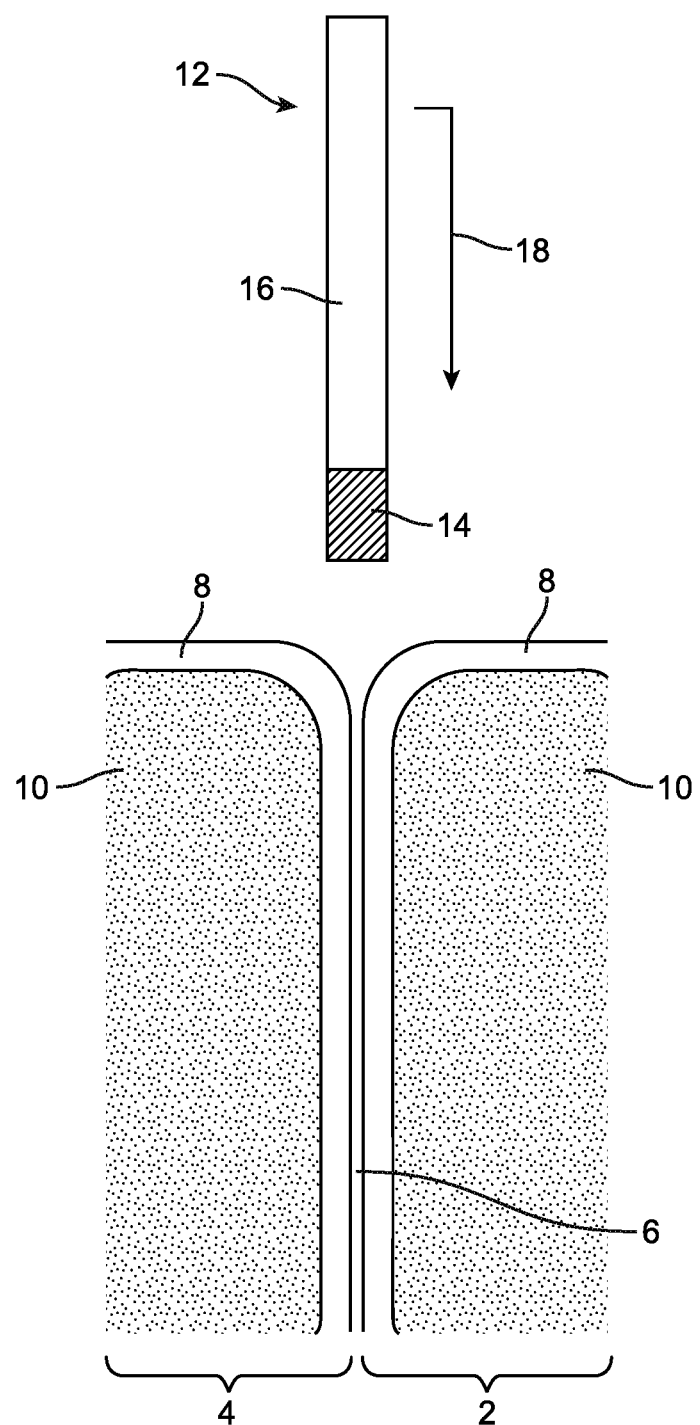
FIGS. 3A-3G illustrate aspects of a stabilization prosthesis deployment from a posterior approach.
Figure 3B:
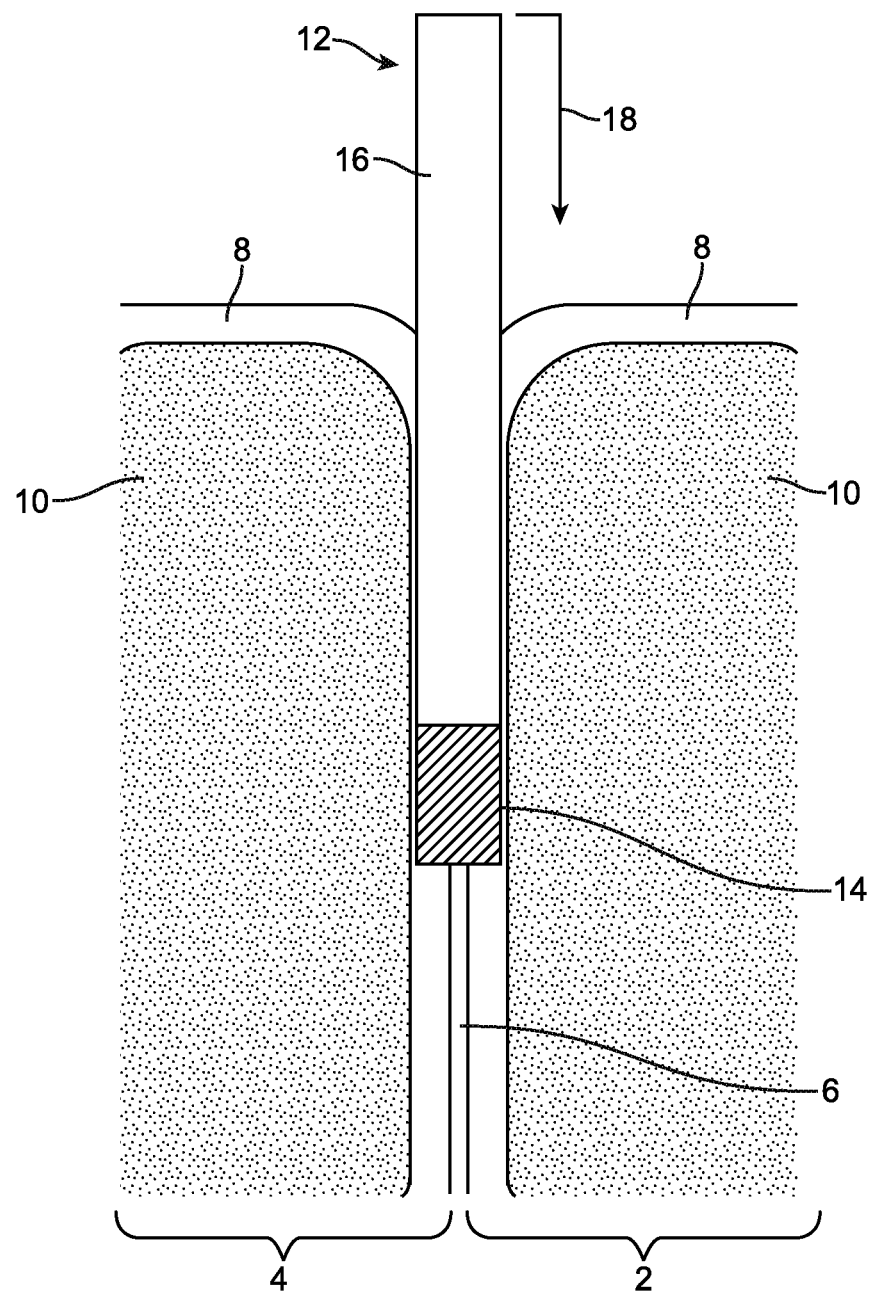
Figure 3C:
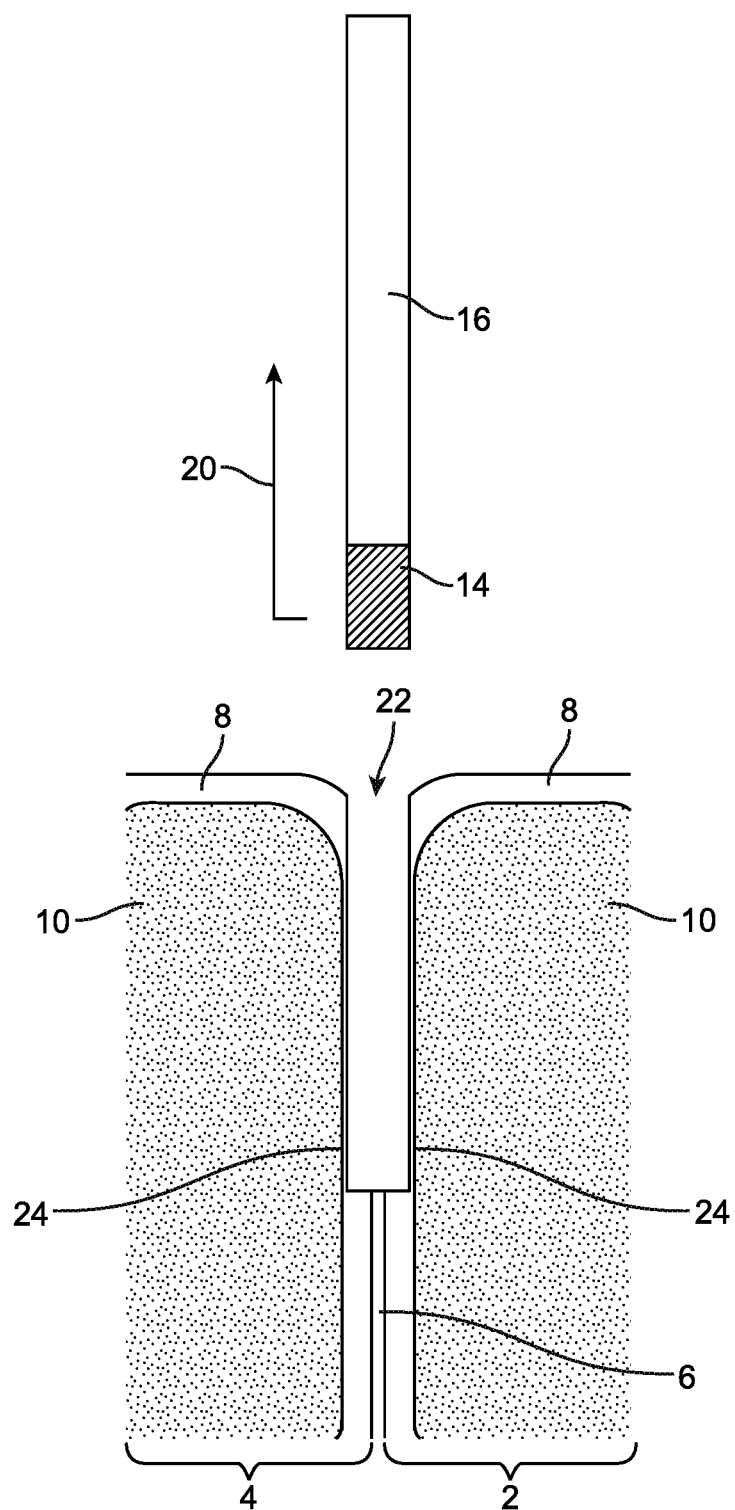
Figure 3D:
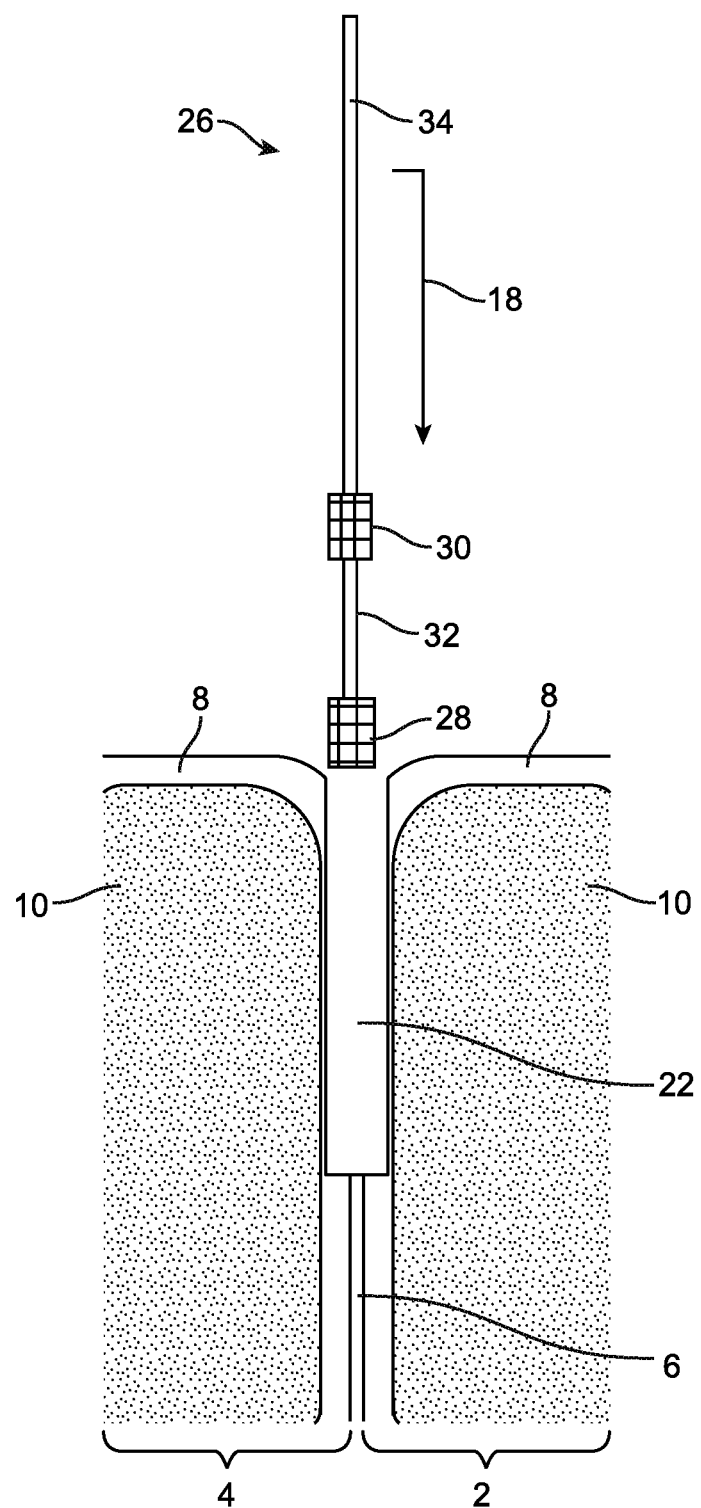
Figure 3E:
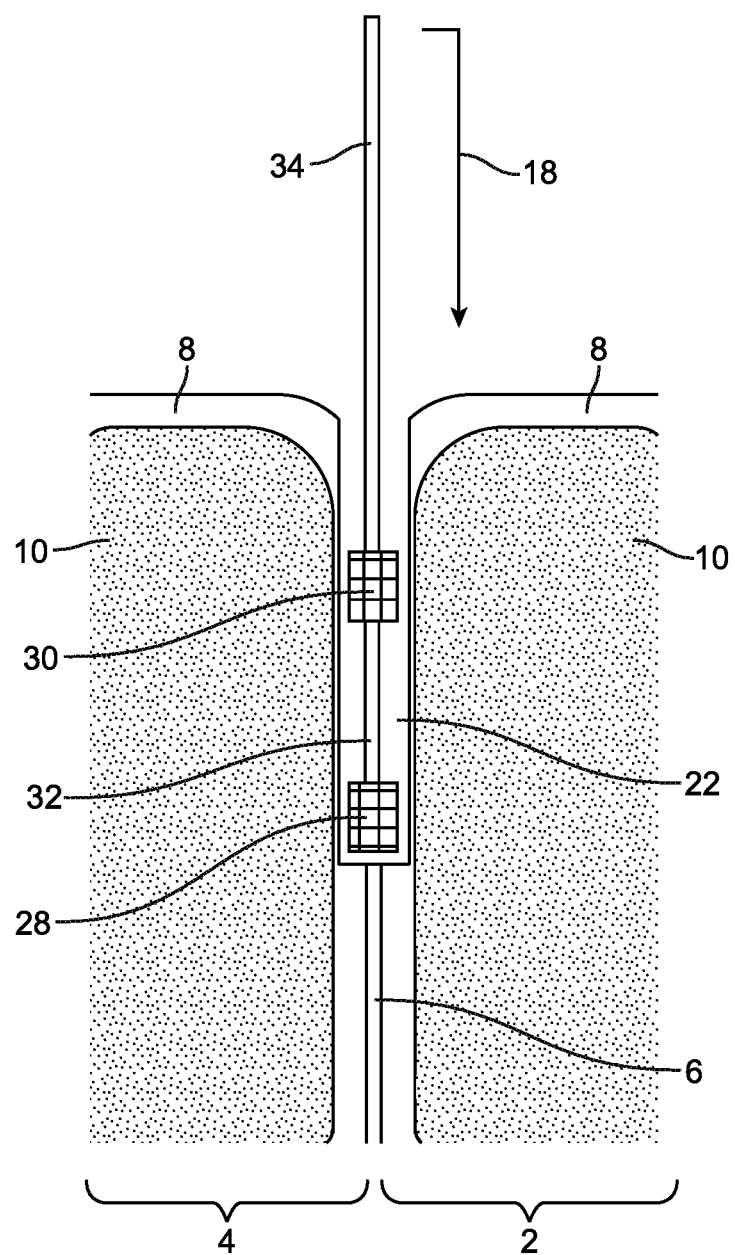
Figure 3F:
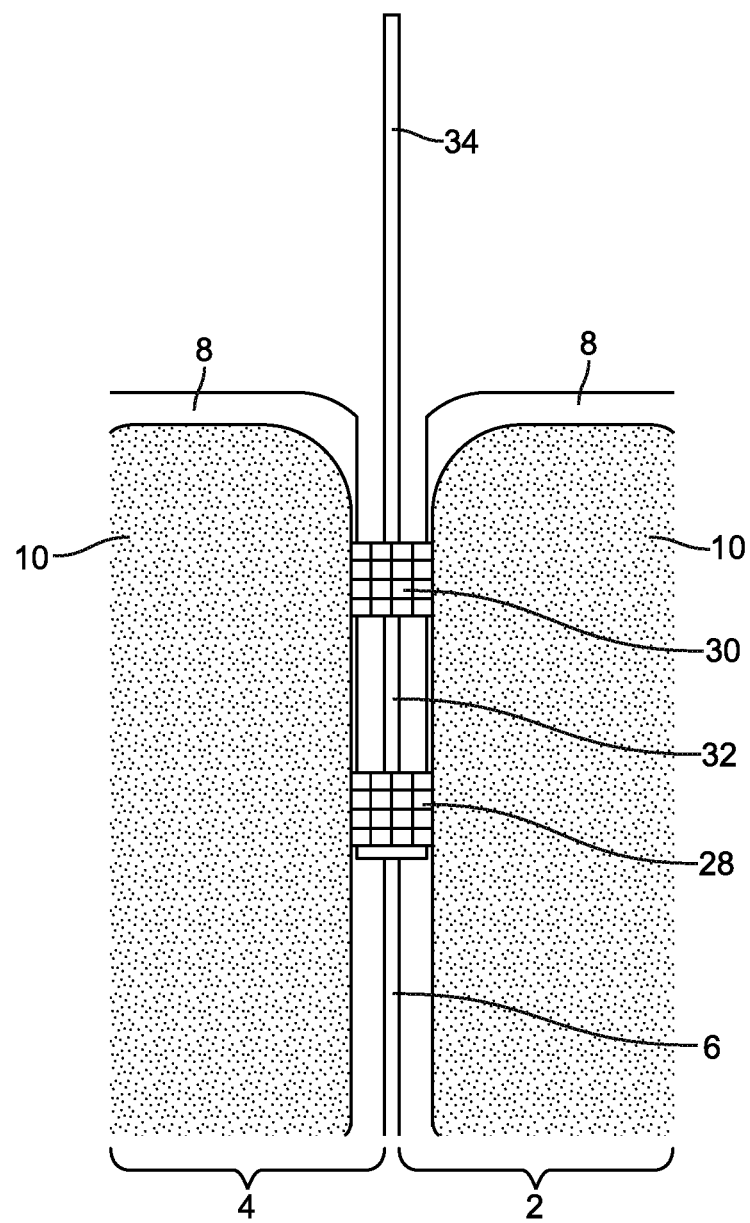
Figure 3G:
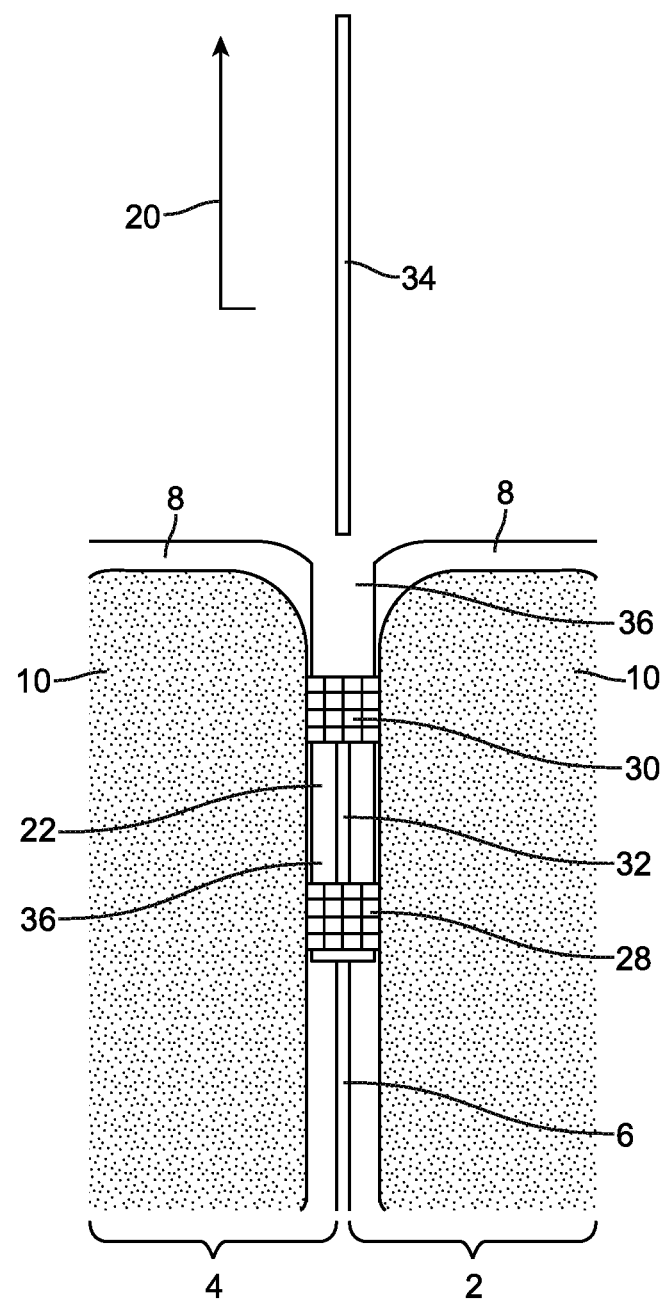

Referring to FIGS. 3A-3G, an SI joint (6) stabilization or fixation embodiment is depicted. As shown in FIG. 3A, a tool assembly (12) comprising an elongate delivery probe (16) and a bone defect-creating distal portion (14) is advanced or inserted (18) from a posterior approach toward an SI joint (6). In one embodiment, the defect-creating distal portion (14) comprises a drill bit which may be operated manually, pneumatically, or electromechanically. In another embodiment, the defect-creating distal portion comprises a coring tool configured to create one or more osteotomies, thereby removing bony material to create a defect. A guide probe (not shown in FIG. 3A; shown as element 206 in FIG. 16A), such as a guidewire or needle, may be utilized to probe minimally invasively into the SI joint (6) to confirm, with the assistance of image capture technologies such as radiography, fluoroscopy, ultrasound, computed tomography ("CT"), magnetic resonance ("MRI"), and the like, that the guide probe has indeed reached the SI joint (6); thereafter other tools and/or assemblies may be advanced using the guide probe as a mechanical guide, such as in known "over the wire" techniques. Alternatively, one or more of the aforementioned imaging modalities may be utilized to observe the position and orientation of the tool assembly (12) itself as it is advanced (18) toward and into the SI joint (6). Referring to FIG. 3B, the tool assembly has been advanced into a desired position, and when removed or retracted (20), as shown in FIG. 3C, leaves behind a defect (22) configured to facilitate placement of a fixation/stabilization prosthesis. In the depicted embodiment, a thin layer of cortical bone (8) preferably remains at least in some aspects of the defect (22), to define the defect volume. In another embodiment, the cortical bone (8) is substantially removed, leaving trabecular bone material (10) to substantially define the defect volume. Referring to FIG. 3D, a prosthesis delivery assembly (26) is advanced (18) into the defect (22). The prosthesis delivery assembly (26) may comprise a distal expandable member (28) coupled by an interconnect member (32) to a proximal expandable member (30), which may be removably coupled to an elongate delivery probe (34) using a coupling which is threaded, latched, controllably fracturable or breakable, or controllably erodible (such as by the techniques described in U.S. Pat. No. 5,122,136, which is incorporated by reference herein in its entirety). The proximal (30) and distal (28) expandable members may comprise porous structures such as small expandable cages, rolls of material, or expandable meshes, such as stent-like structures, which may be controllably expanded once in position using means such as hydraulic pressure and expandable balloon lumens. Such expandable members (28, 30) may also be self-expanding, subsequent to release of a binding member, such as a small circumferential tensile member configured to be controllably erodible, breakable, untie-able, or fracturable from a proximal control location by the operator. Referring to FIG. 3E, the expandable members (28, 30) are in a deployment position within the defect (22). Referring to FIG. 3F, the expandable members (28, 30) have been expanded. In the depicted embodiment, such expansion has intentionally expanded the outer dimensions of the expandable members beyond the previous outer dimensions of the defect (22), thus, creating a substantially interlocked interface between the bones (2, 4) and prostheses members (28, 30, 32). Referring to FIG. 3G, the elongate delivery probe is retracted (20), leaving the deployed prosthesis in place. Other materials may also be deployed into the fixation/stabilization environment to catalyze or facilitate mechanical and/or biological fixation, including but not limited to demineralized bone matrix, autograft bone material, allograft bone material, polymethylmethacrylate, calcium-based bone void filler material, and bone morphogenic protein, such as the varieties known by the names "BMP-1", "BMP-7", and "OP-1". In one embodiment, one or more of such materials are contained within the expandable members (28, 30) when they are deployed.

Figure 4A:
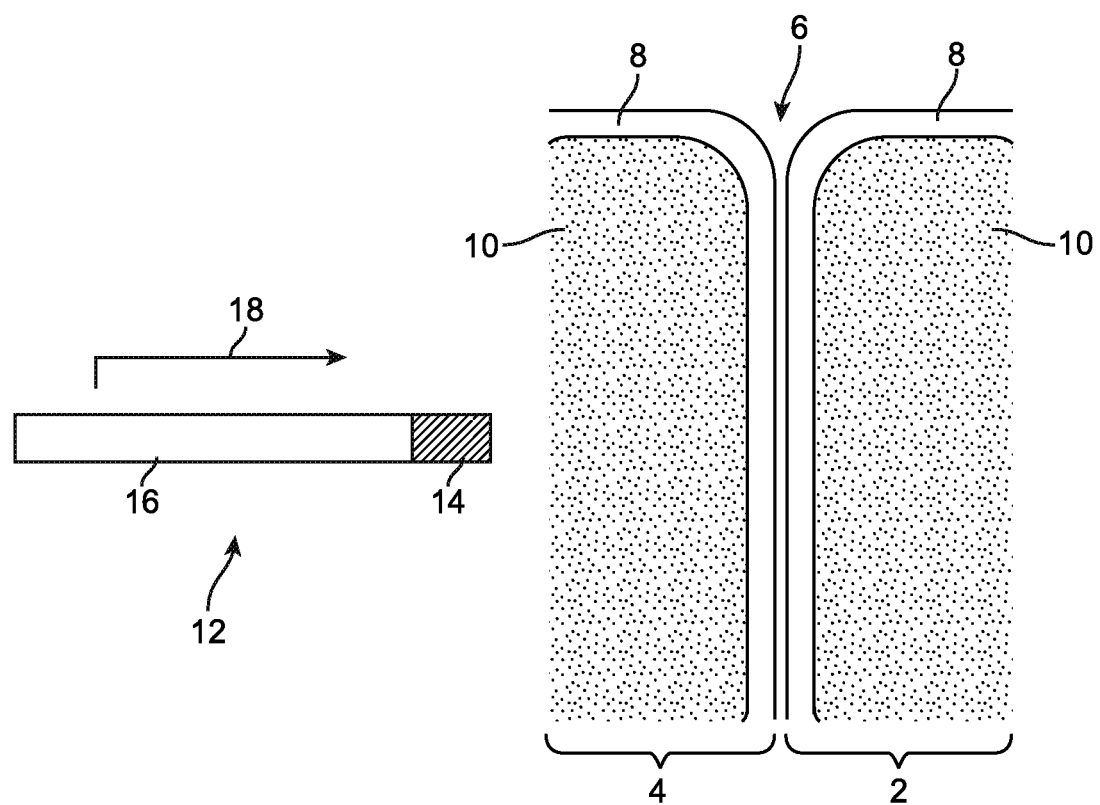
FIGS. 4A-4G illustrate aspects of a stabilization prosthesis deployment from a lateral approach.
Figure 4B:
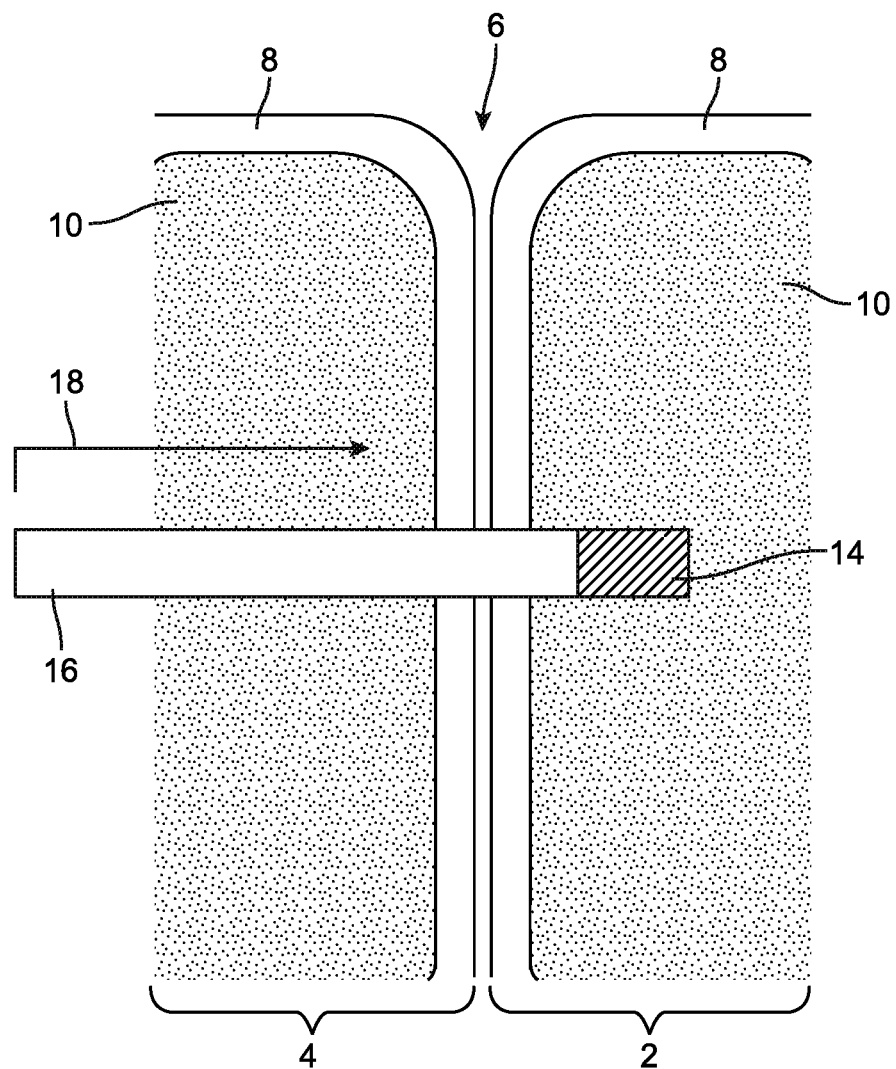
Figure 4C:
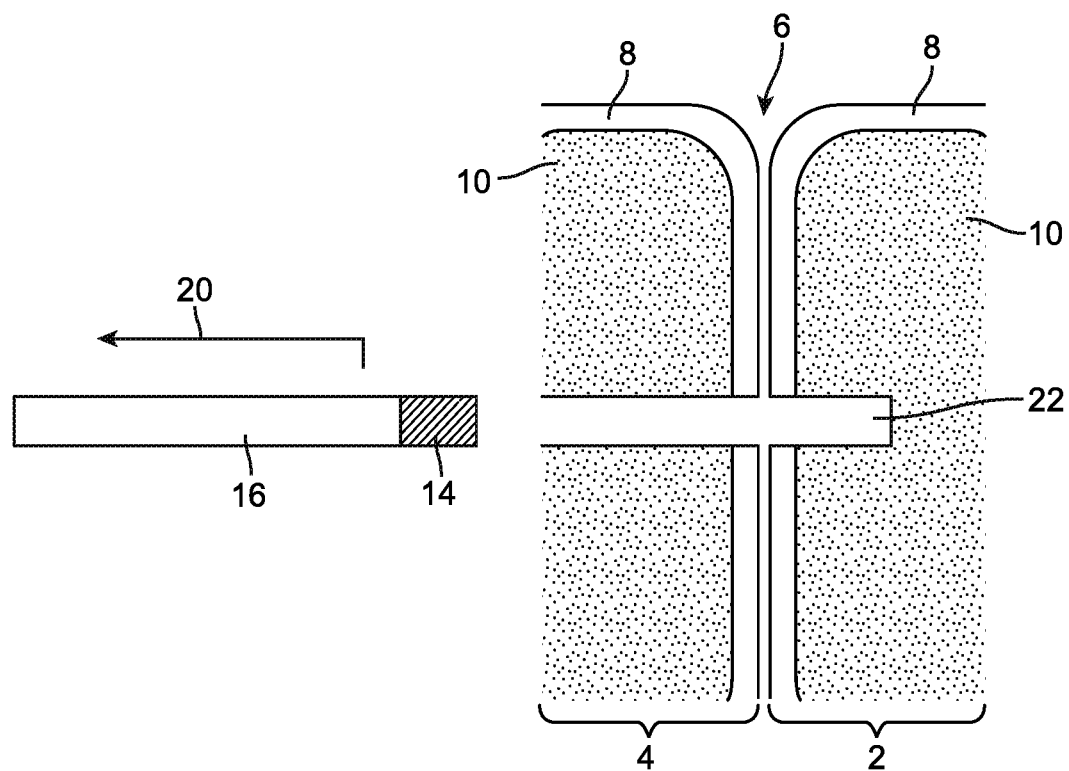
Figure 4D:
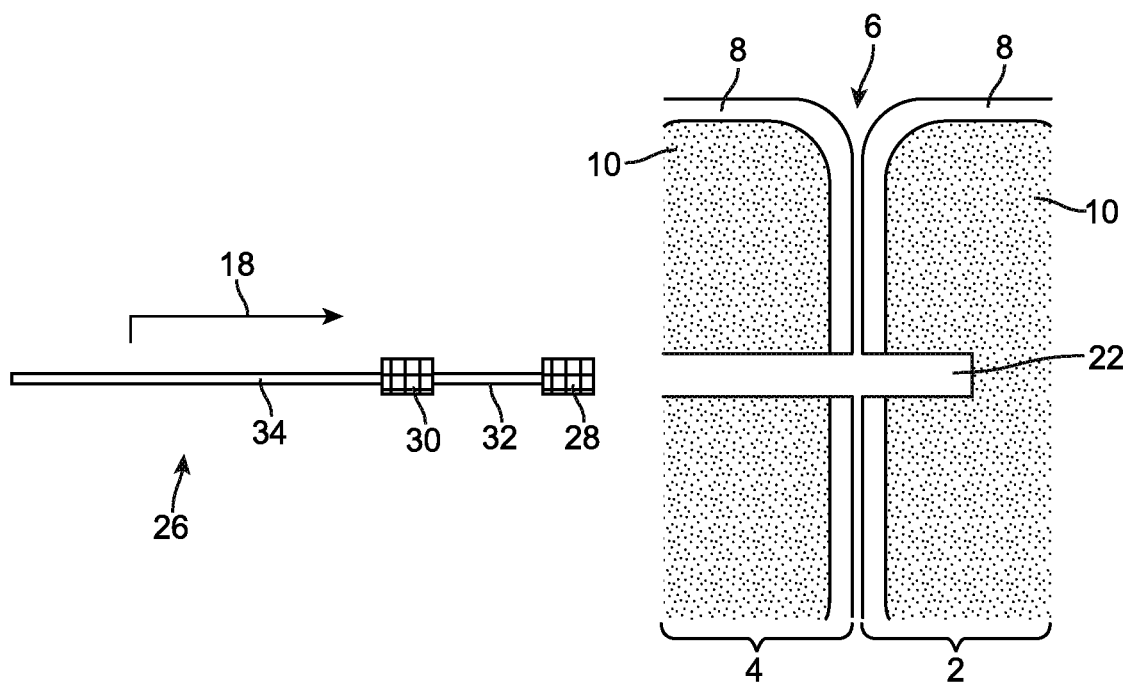
Figure 4E:
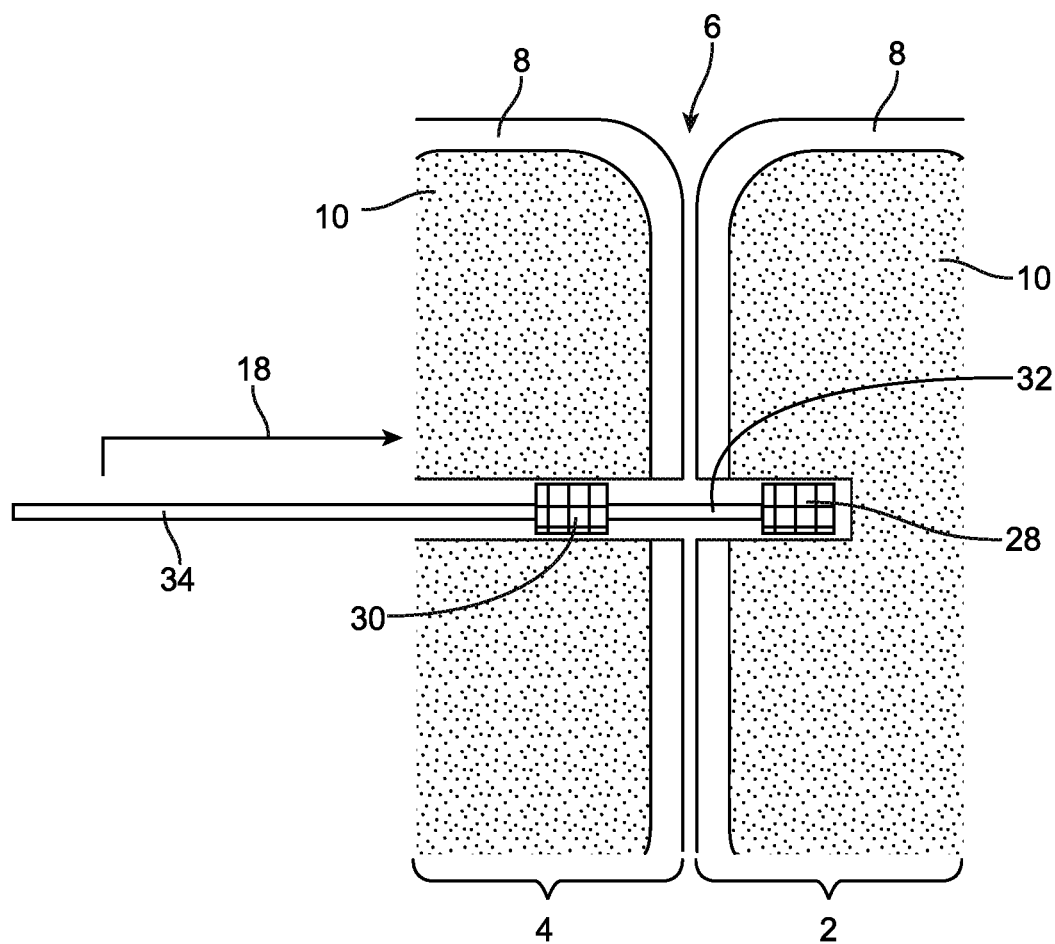
Figure 4F:
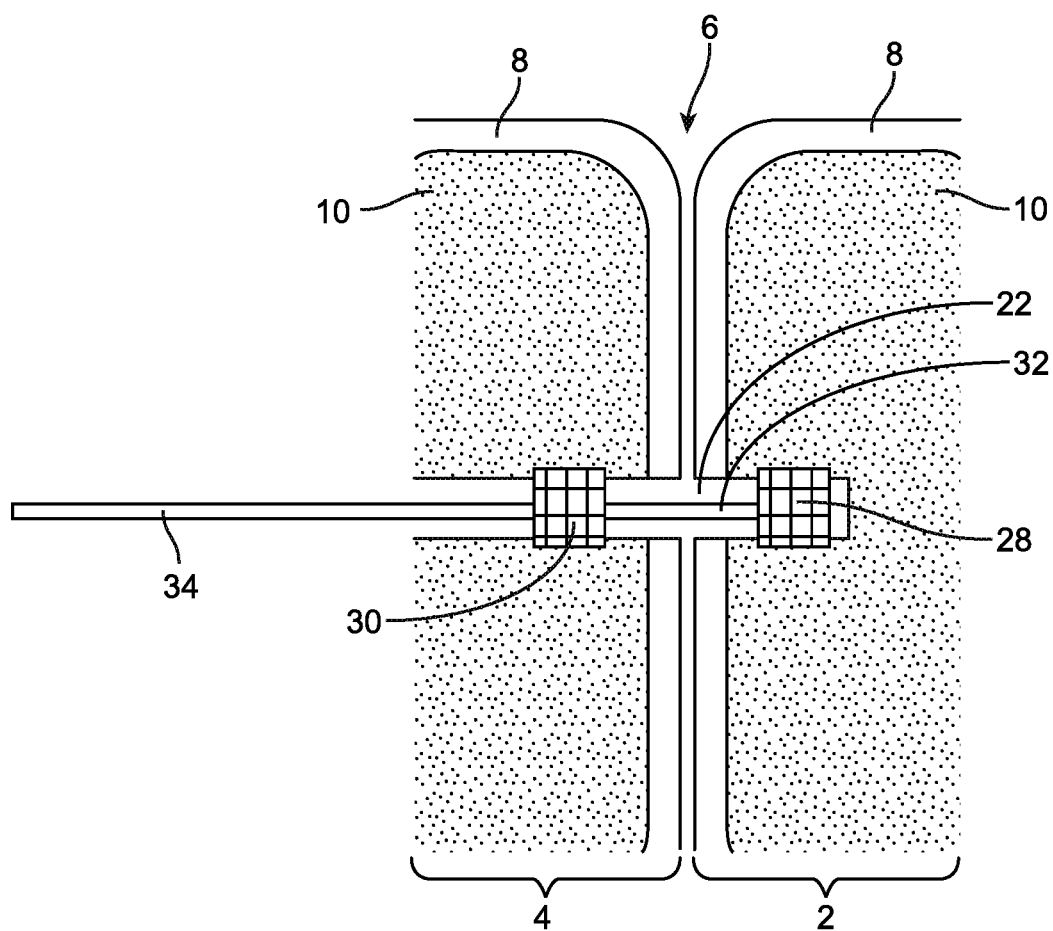
Figure 4G:
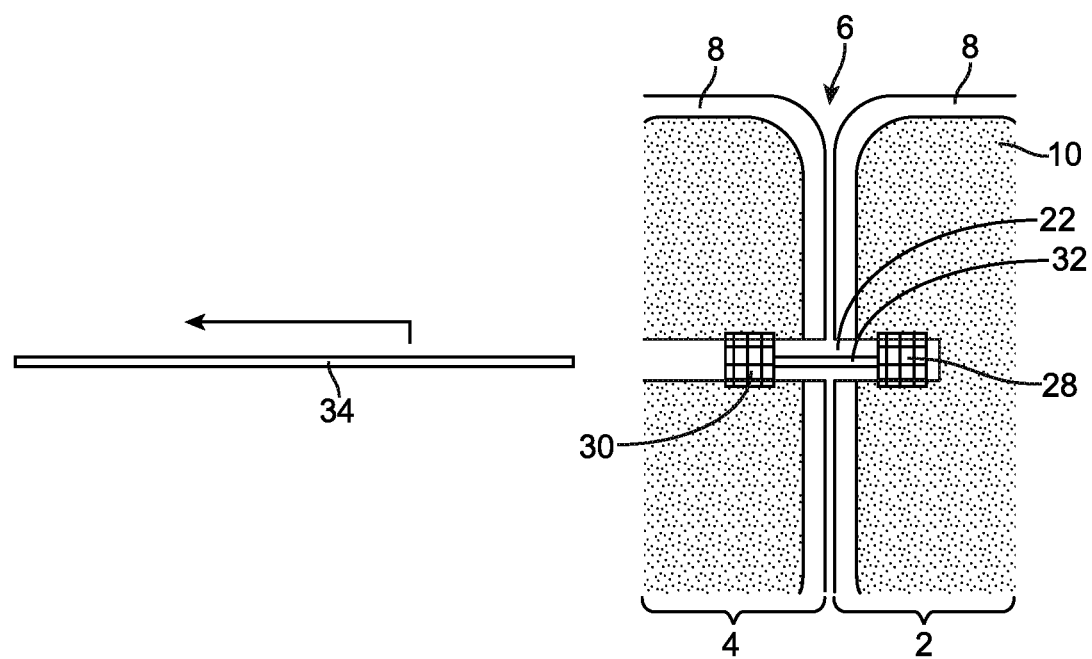

Referring to FIGS. 4A-4G, an analogous configuration may be utilized from a lateral approach to fix or stabilize an SI joint (6). As shown in FIG. 4A, a tool assembly (12) is advanced (18) from a lateral approach, and may be utilized to create and leave behind a defect (22) after retraction (20), as shown in FIGS. 4B-4C. As shown in FIGS. 4D-4G, the expandable members (28, 30) may be utilized along with the interconnecting member (32) to place the SI joint (6) at least partially in stabilizing lateral compression. Indeed, in one embodiment suitable for use from a posterior or lateral approach, the interconnect member (32) may be remotely adjustable in length, such as by turning the delivery probe (34) relative to the deployed prosthesis assembly (28, 30, 32) to rotate a threaded interface, to controllably create tension in the interconnect member (32), and thereby compression in at least portions of the couple bony structures (2, 4).

Figure 5A:
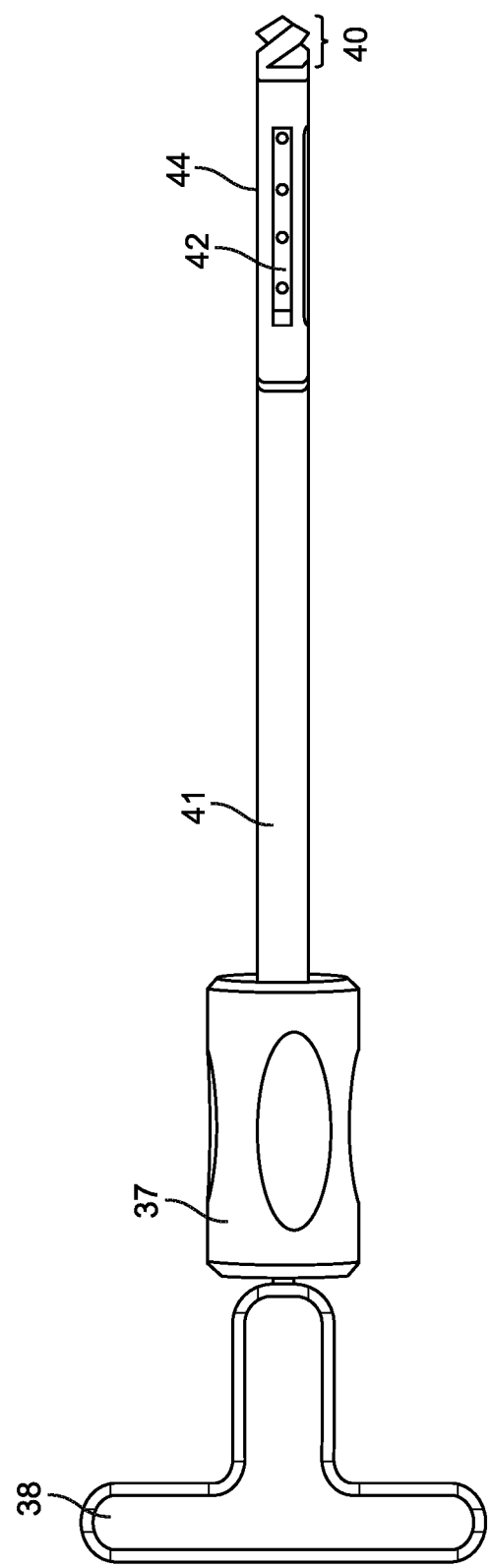
FIGS. 5A-5J illustrate aspects of stabilization prosthesis deployments from both posterior and lateral approaches.
Figure 5B:
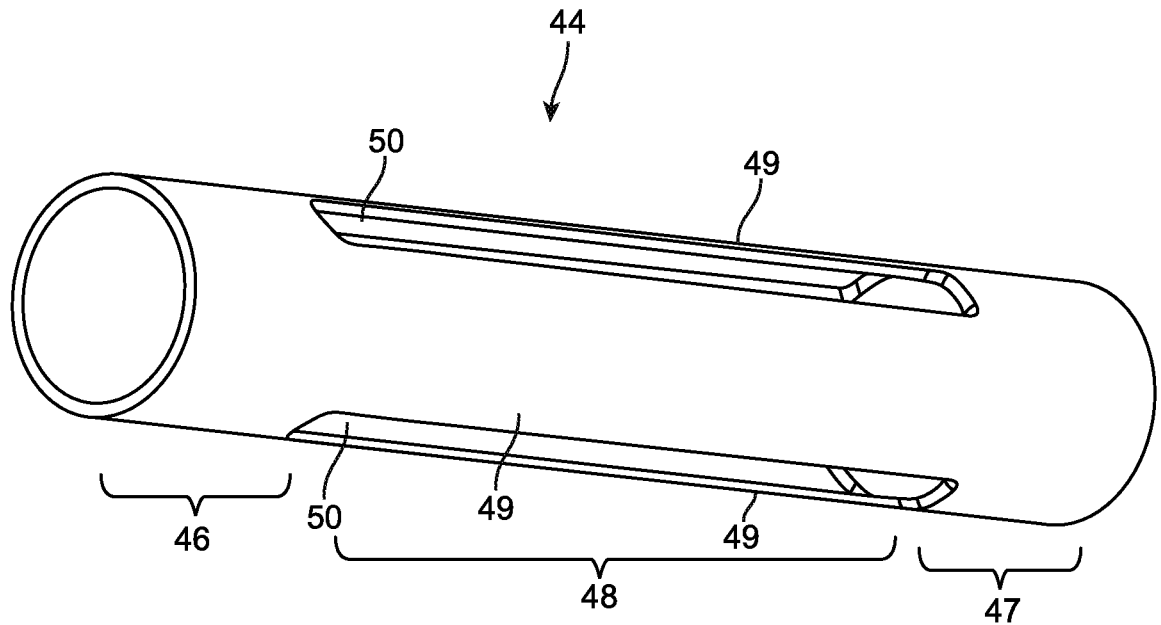
Figure 5C:
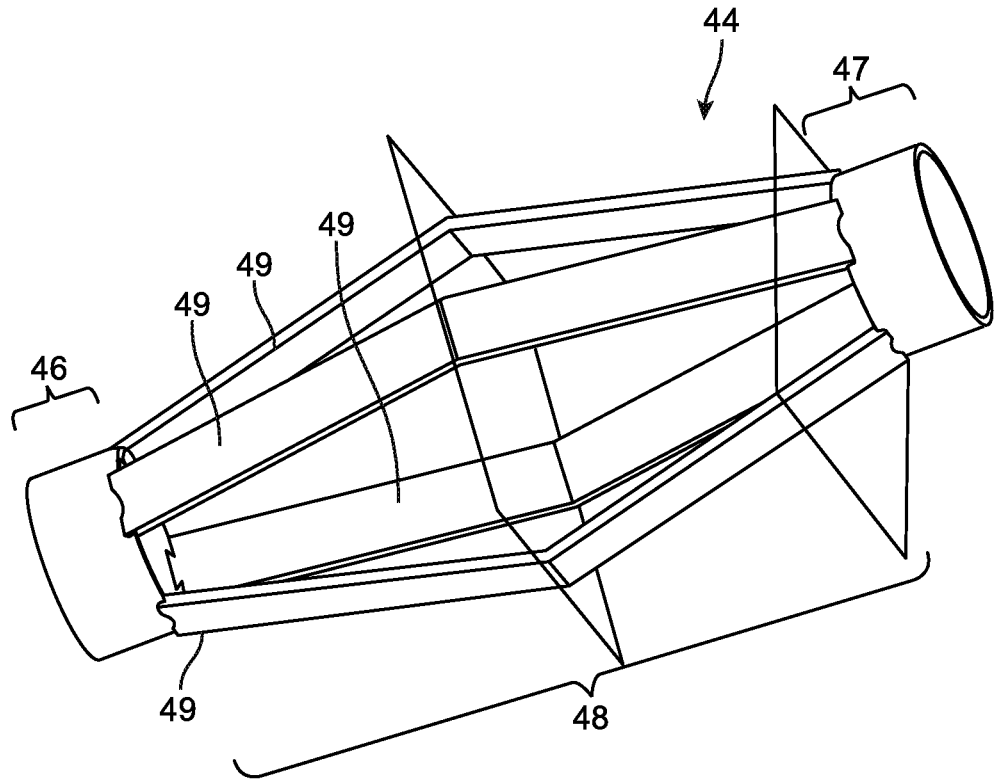
Figure 5D:
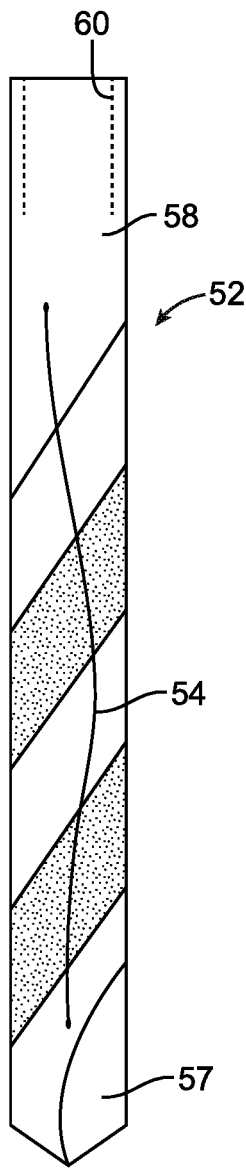
Figure 5E:
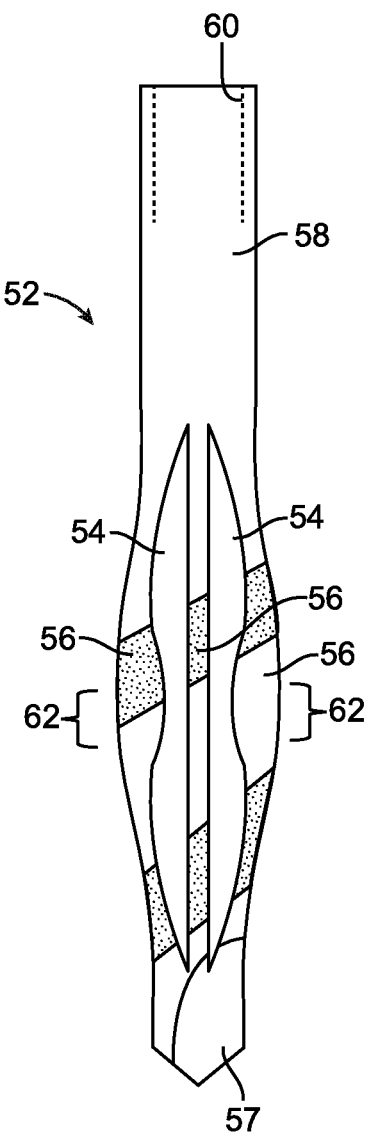
Figure 5F:
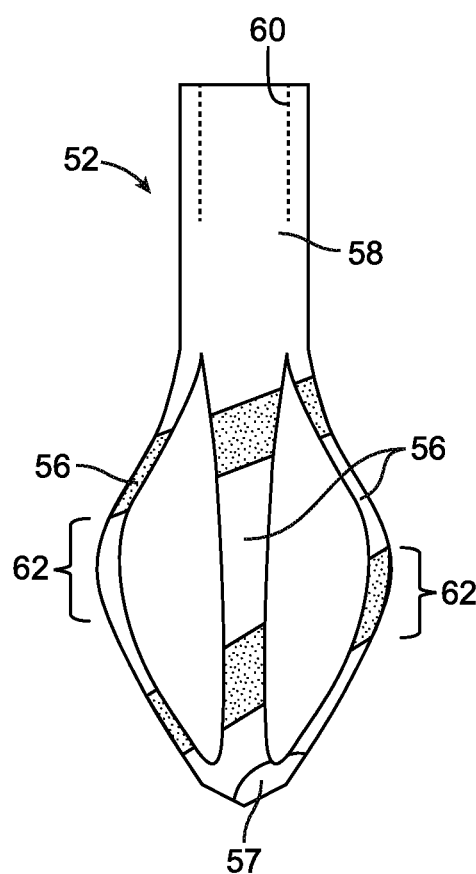

Referring to FIG. 5A, a prosthesis deployment and defect creation assembly is depicted having a distal portion (40) configured to drill or core through bony material, providing a defect volume through which an expandable prosthesis (44) may be advanced. Once in position, which may be confirmed as described above using various intraoperative imaging modalities, relative rotation and/or linear deflection between two handles (37, 38) may be utilized to pull the distal portion (40), through a tension member (42), toward the elongate shaft (41), thereby putting the expandable prosthesis (44) in compression, and ultimately pulling the distal portion through the center of the prosthesis (44), leaving behind a deployed expanded prosthesis, as shown, for example, in FIG. 5C and FIGS. 5G-5J. FIGS. 5B and 5C illustrate close-up orthogonal views of an embodiment of an expandable prosthesis having end portions (46, 47), and a slotted midportion (48), with slots (50) that complementarily define defectable elongate members (49) configured to yield and bend outward, as shown in FIG. 5C, when the end portions (46, 47) are compressed toward each other. Referring to FIGS. 5D-5F, another embodiment is depicted wherein centrifugal forces associated with angular velocity may be utilized to expand a drilling member prosthesis, shown in compact form in FIG. 5D, to expand to an expanded form, as shown incrementally in FIGS. 5E and 5F. The proximal portion (58) is configured without defects and has a releasable coupling, such as a threaded coupling (60), for mechanical interfacing with a rotation/insertion drive shaft (not shown). Below a designed angular velocity threshold, the drilling member prosthesis (52) functions as a drill bit and may be rotated and advanced to create a defect and be positioned to a preferred location within or adjacent to bony tissue. When in position, as may be confirmed, for example, using the aforementioned imaging modalities, the operator may elect to expand/deploy the prosthesis by exceeding the angular velocity threshold, thus, causing the relatively large massed central portions (62) of connecting members (56) formed by the defects (54) to migrate outward, thereby expanding the overall radius of the prosthesis (52), as shown in FIG. 5F. Such a configuration may also be used in installations such as those depicted in FIGS. 5G-5J.

Figure 5G:
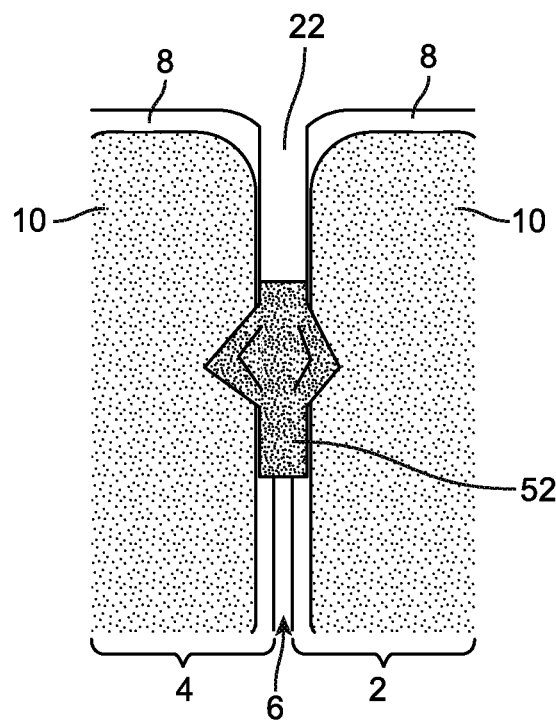
Figure 5H:
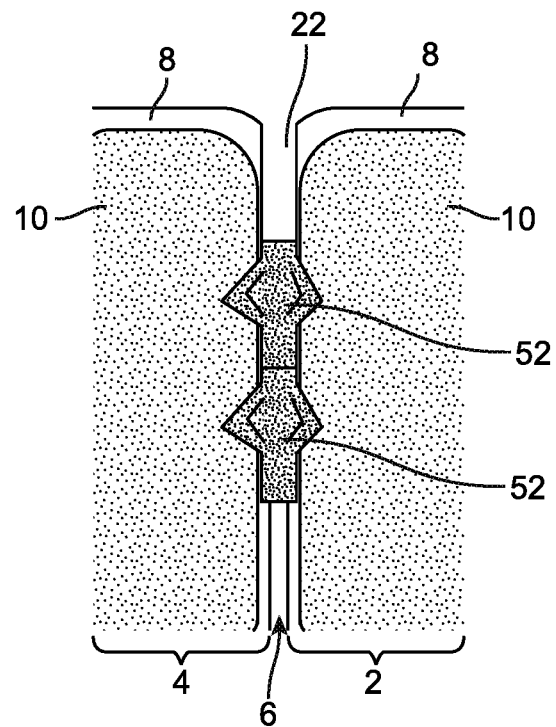
Figure 5I:
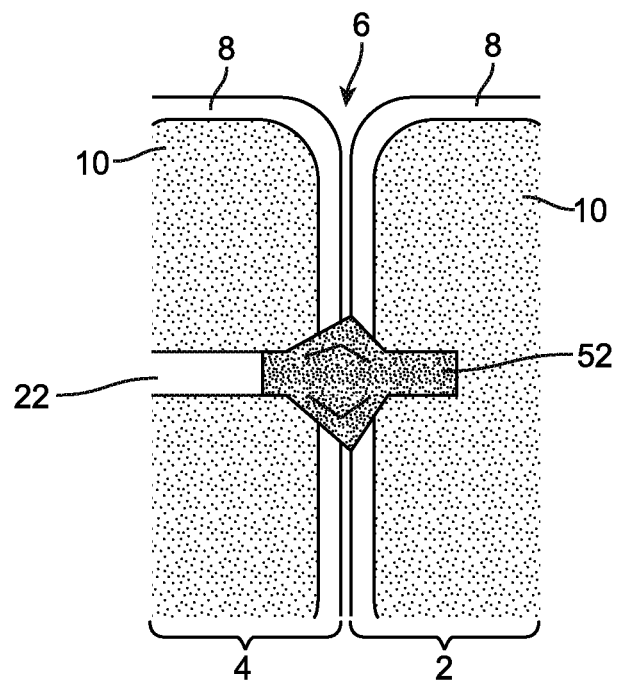
Figure 5J:
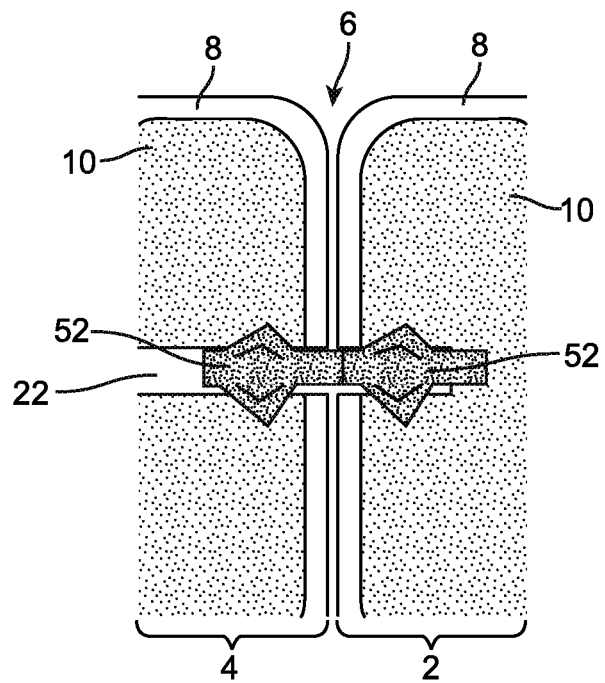

Referring to FIG. 5G, a single radially expandable prosthesis (52) is deployed from a posterior approach to stabilize or fixate an SI joint (6). Referring to FIG. 5H, two radially expandable prostheses (52) are deployed from a posterior approach to stabilize or fixate an SI joint (6). In one embodiment, they may be coupled with a tensile or stabilizing interconnect member (not shown). In another embodiment, they may simply reside adjacent one another. Referring to FIGS. 5I and 5J, analogous deployment embodiments are illustrated from a lateral approach.

Figure 6A:
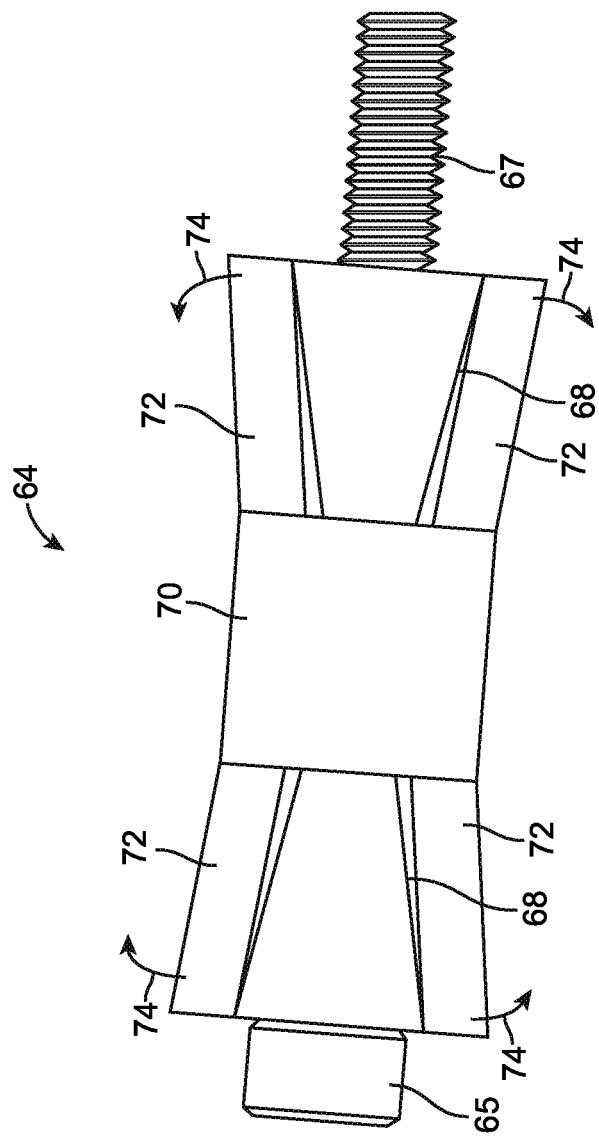
FIGS. 6A-6E illustrate aspects of stabilization prosthesis deployments from both posterior and lateral approaches.
Figure 6B:
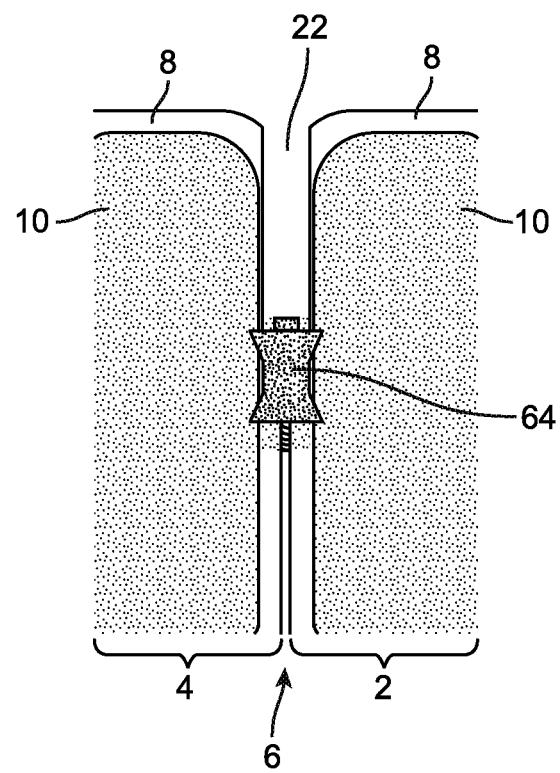
Figure 6C:
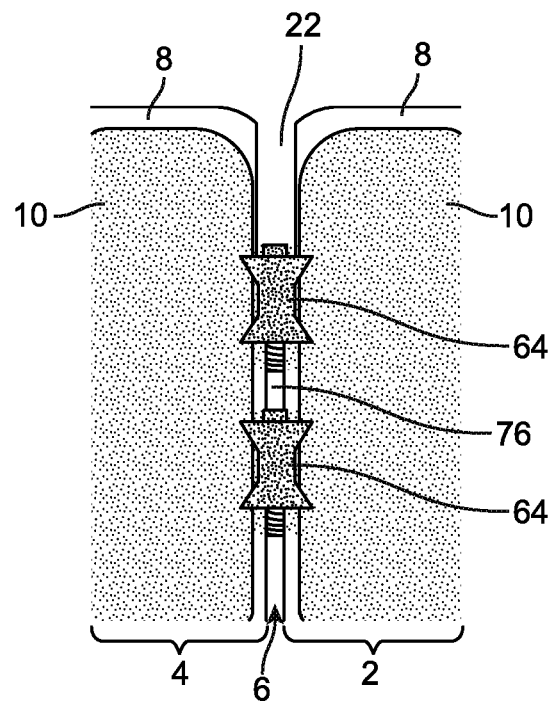
Figure 6D:
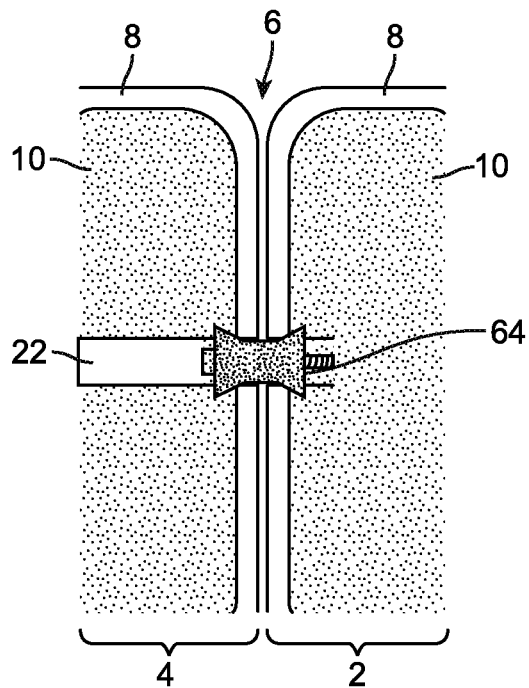
Figure 6E:
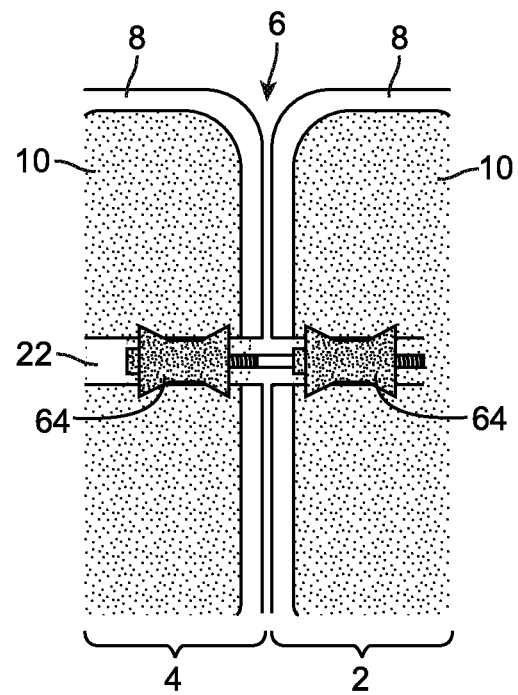

Referring to FIG. 6A, another expandable prosthesis assembly (64) is depicted, comprising a main body (70) coupled to four leg members (72) which are configured to bend and rotate away from the main body (70) when two wedge members (68) are advanced toward each other with the use of a screw comprising a threaded shaft (67) and screw head (65); preferably one or both of the wedge members have a threaded interface with the screw shaft (67) to provide advancement of the wedge members (68) relative to each other when the screw shaft (67) is rotated relative to the wedge members (68) and body (70) using an actuator or manual rotational driver interfaced with the screw head (65). Referring to FIG. 6B, subsequent to creation of a defect (22) utilizing configurations such as those described in reference to FIG. 3B, and expandable prosthesis assembly (64) may be advanced into place and controllably expanded to stabilize the SI joint (6). Referring to FIG. 6C, one or more such assemblies (64) may be utilized, and they may be coupled together with an intercoupling member (76), which may be controllably elongated or decreased in dimension, as described above, to create tension or compression in the surrounding bony structures. Referring to FIGS. 6D and 6E, analogous configurations are depicted utilizing a lateral approach.

Referring to FIGS. 7A-10B, several coring or osteotome tool embodiments are depicted; they may be utilized from posterior or lateral approaches to create defects which may be subsequently occupied by one or more prosthesis components to stabilize or fix an SI joint.

Figure 7B:
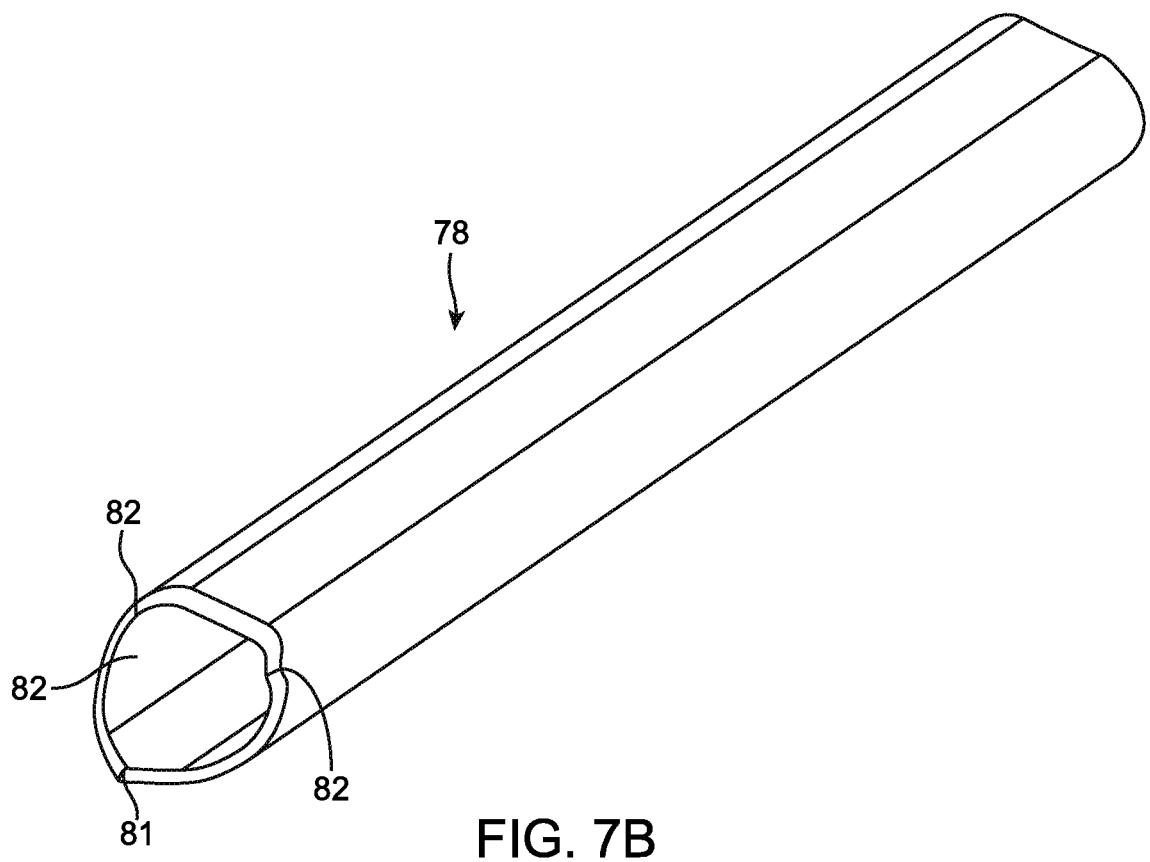
FIGS. 7A-7B illustrate aspects of a defect-creating tool assembly.
Figure 7A:
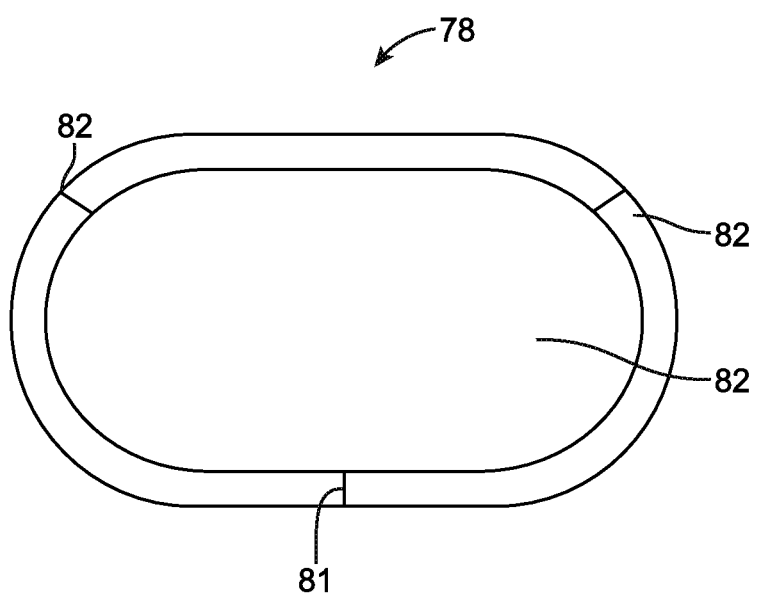

Referring to FIG. 7B, a three-leading point osteotome (78) embodiment is depicted having one advanced lead point cutting apex (81) and two following lead point cutting apices (82) located distally. A lumen or recess (82) is defined through the middle of the osteotome (78) to contain captured bone tissue. Referring to FIG. 7A, a straight end view shows that the osteotome (78) embodiment of FIG. 7B has a generally oval cross sectional shape. The lead point cutting apices (81, 82) are configured to assist with positioning, orienting, and generally advancing the osteotome (78) as it accesses and traverses the bony structures comprising an SI joint.

Figure 8A:
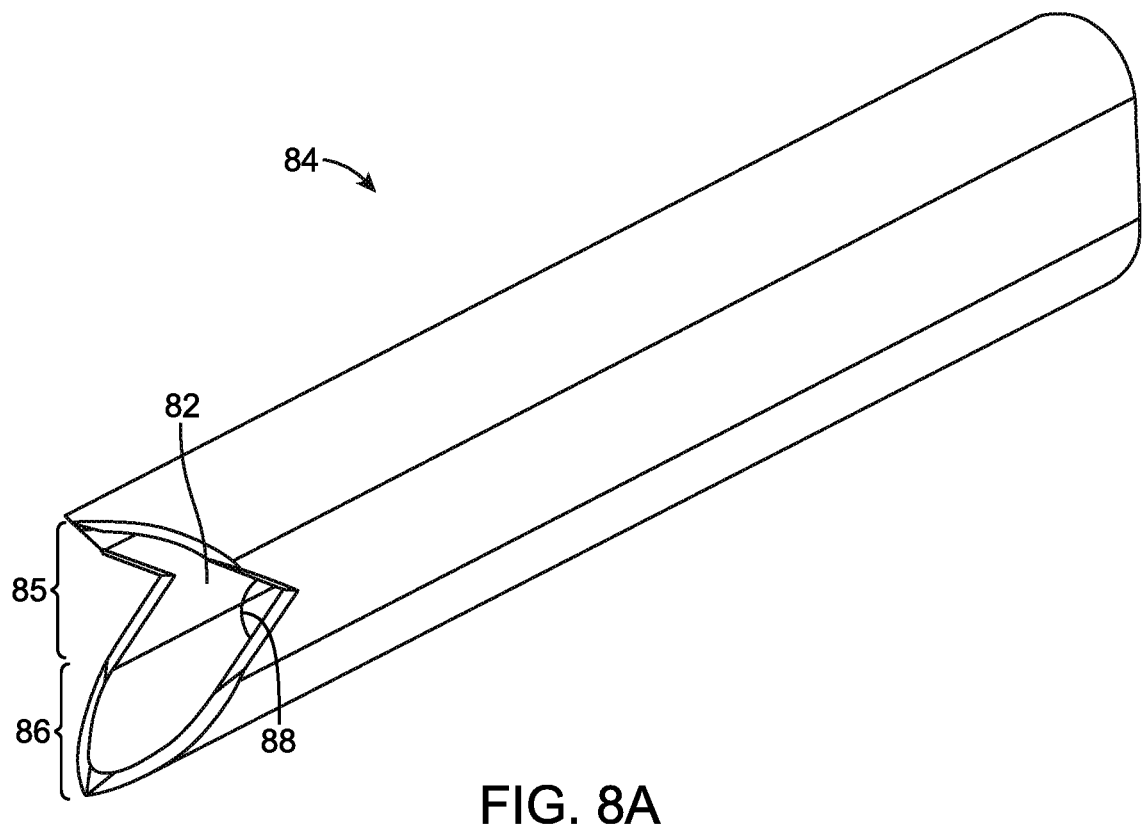
FIGS. 8A-8B illustrate aspects of a defect-creating tool assembly.
Figure 8B:
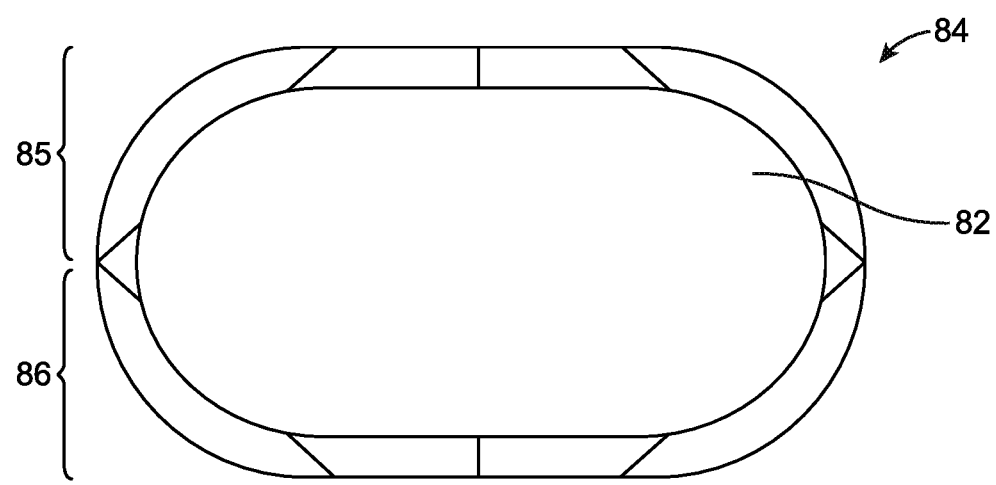

Referring to FIG. 8A, a two jawed osteotome (84) embodiment is depicted having a first jaw portion (85), a second jaw portion (86), an included jaw angle (88), and a defined lumen or cavity (82), all of which are configured to create controlled defects at the SI joint. As shown in the straight end view of FIG. 8B, this embodiment also has a generally oval cross sectional shape.

Figure 9A:
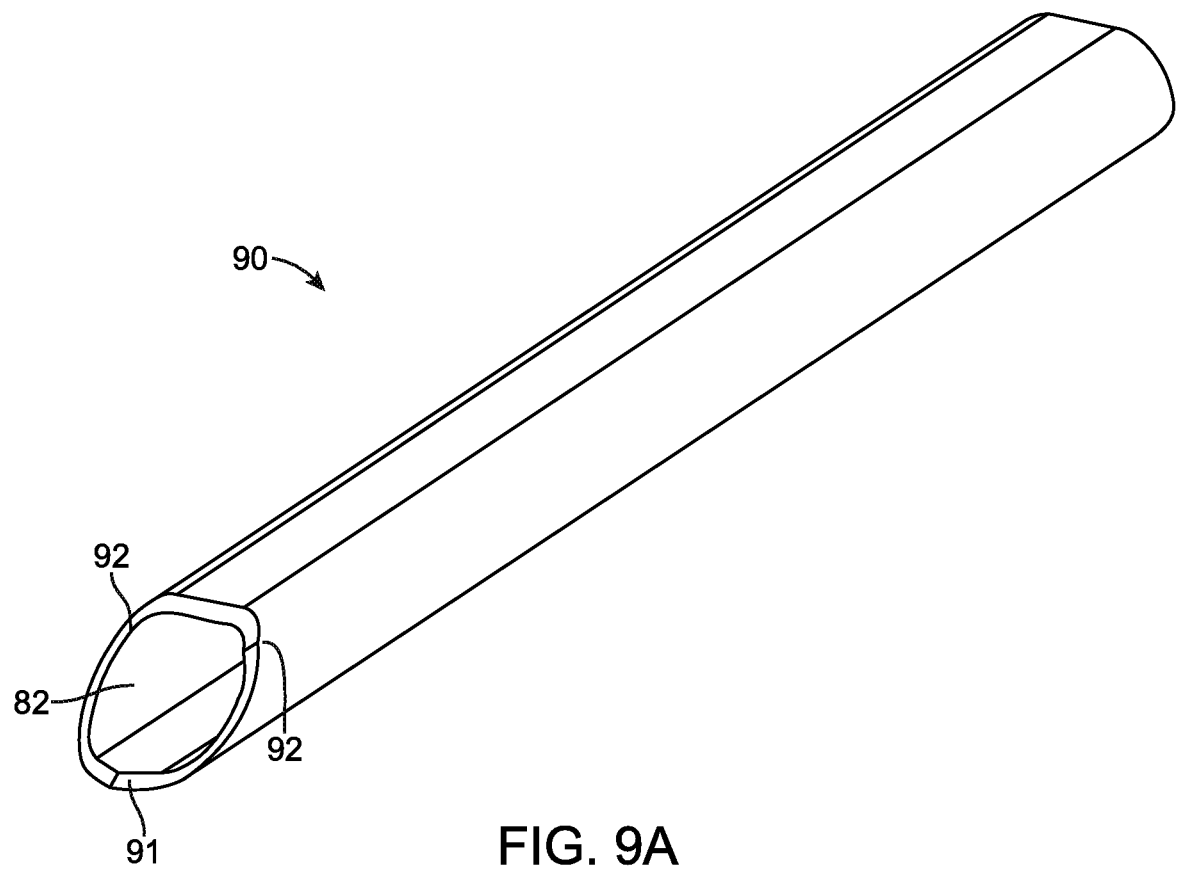
FIGS. 9A-9B illustrate aspects of a defect-creating tool assembly.
Figure 9B:
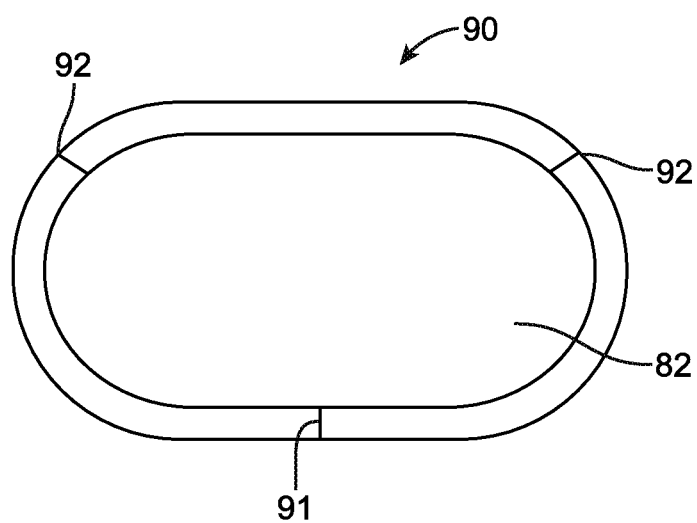

Referring to FIG. 9A, an embodiment similar to that of FIG. 7A is depicted, with the exception that the distal taper angle and cutting apices (91, 92) are milder geometrically. The straight end view of FIG. 9B shows that this embodiment also has a generally oval cross sectional shape.

Figure 10A:
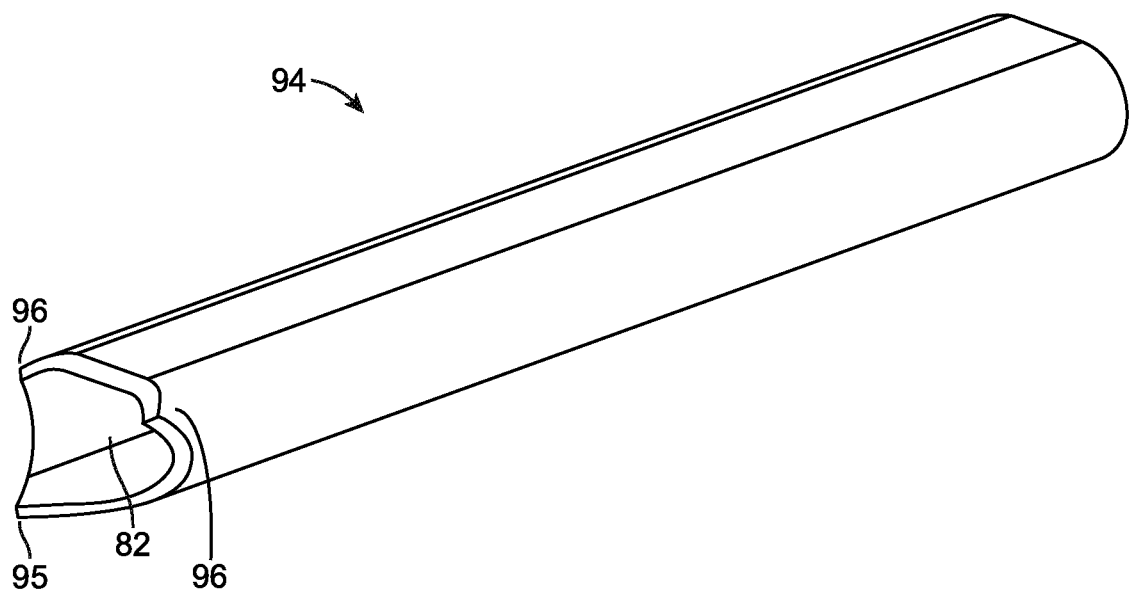
FIGS. 10A-10B illustrate aspects of a defect-creating tool assembly.
Figure 10B:
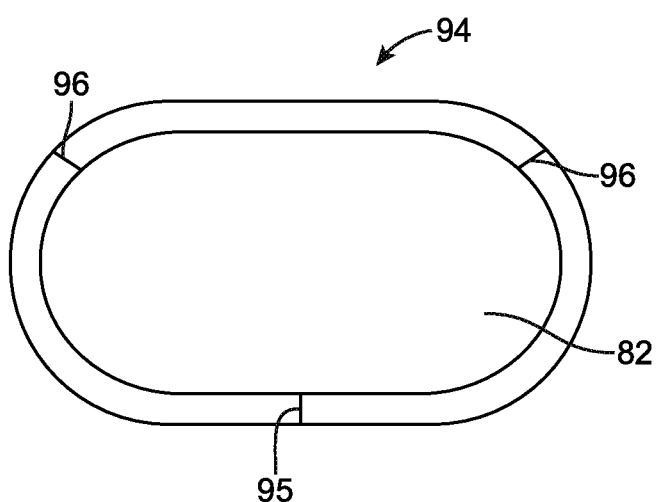

FIG. 10A depicts an embodiment similar to that of FIG. 9A, with the exception that more material has been recessed away in between each of the apices (95, 96), to form more pronounced distal contact points as this osteotome (94) is placed in contact with, and advanced through, bony structures comprising the SI joint. The straight end view of FIG. 10B shows that this embodiment also has a generally oval cross sectional shape.

Figure 11A:
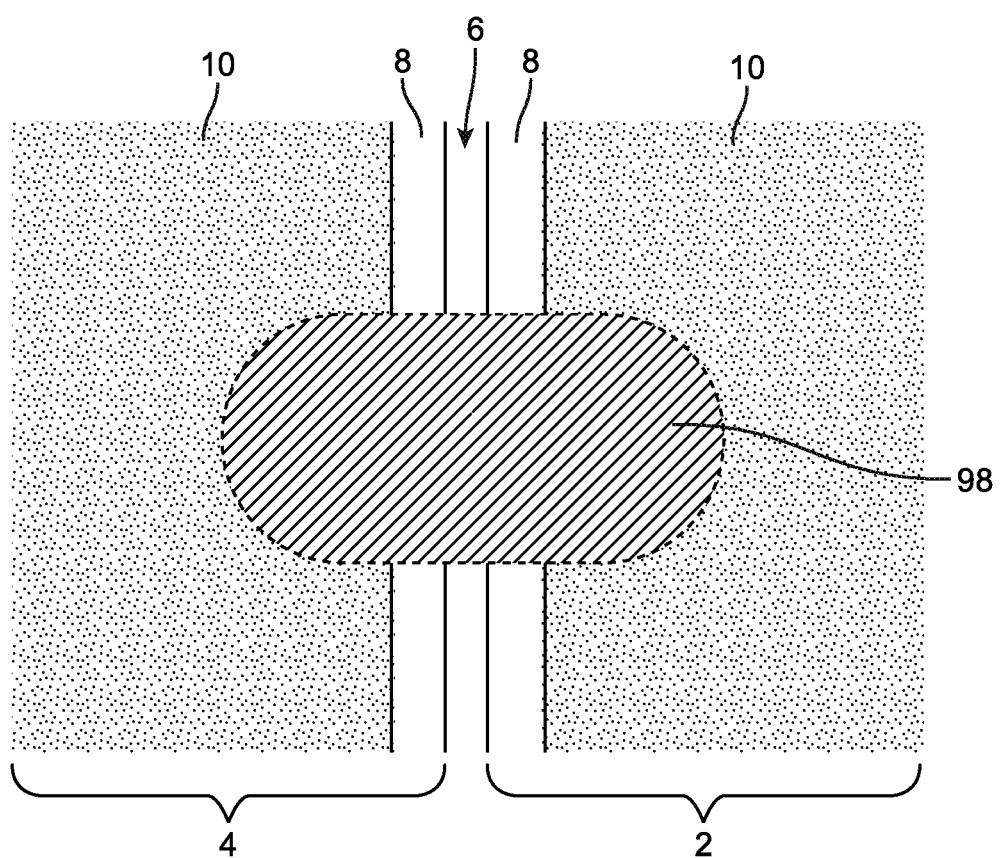
FIGS. 11A-11E illustrate various embodiments of defect-creating paradigms to stabilize the sacro-iliac joint from a posterior approach.
Figure 11B:
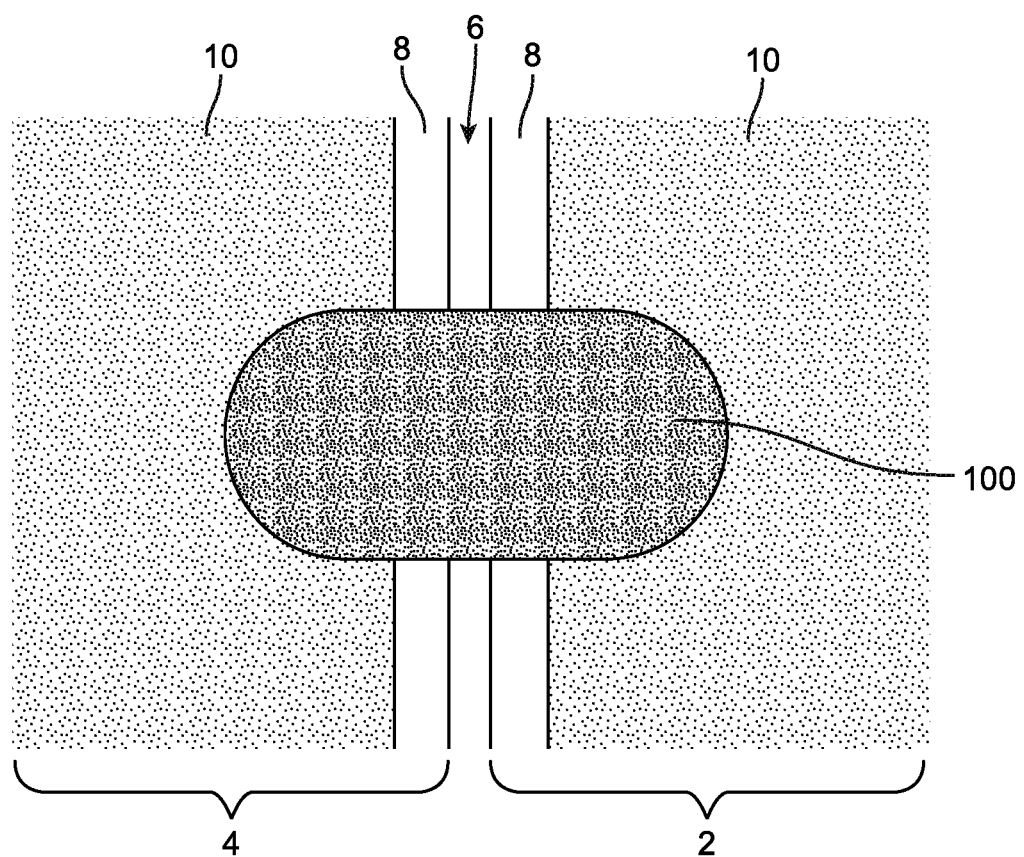
Figure 11C:
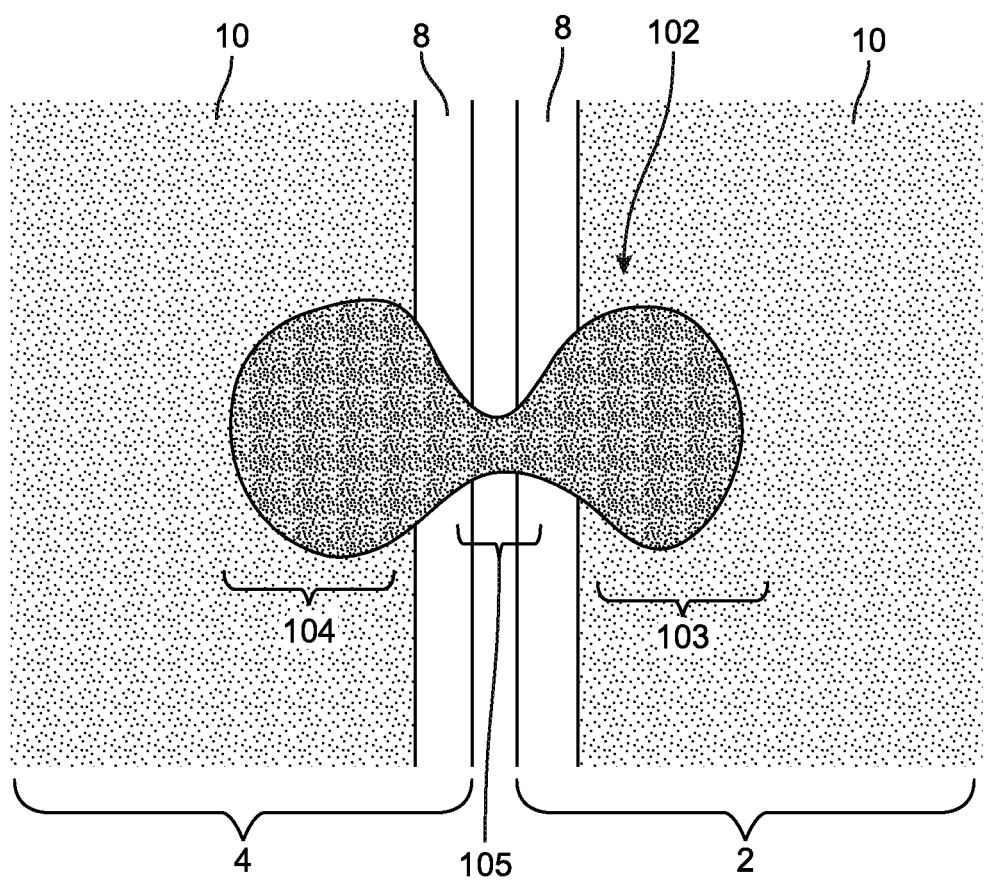
Figure 11D:
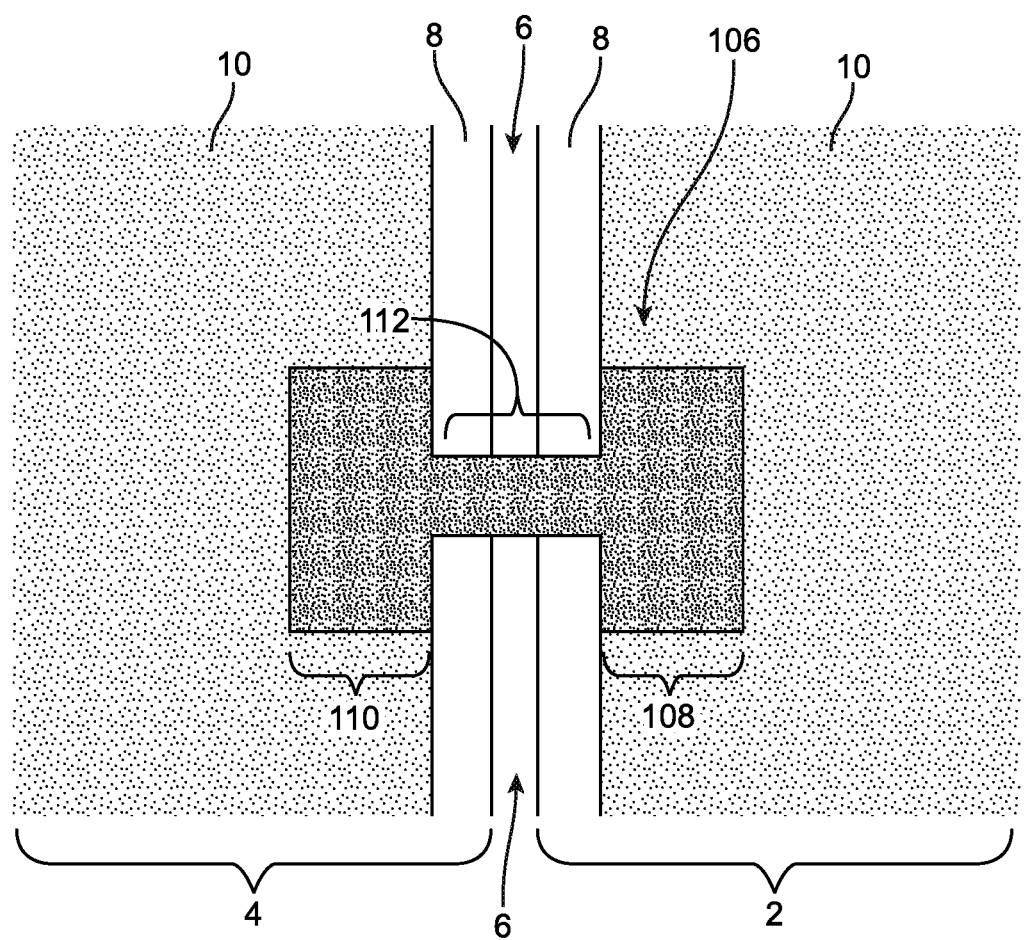
Figure 11E:
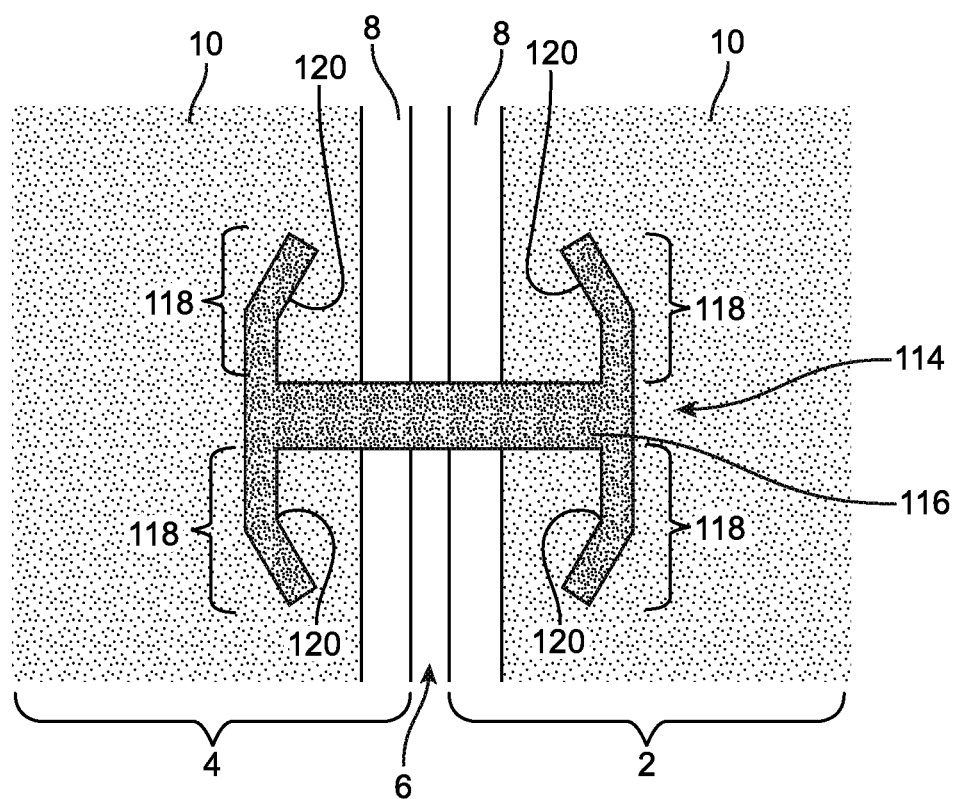

Referring to FIGS. 11A-11E, various osteotome configurations may be utilized to create fixation/stabilization defects of various geometries—and these defects may be subsequently occupied by prostheses configured to stabilize and/or fix the SI joint. Each of the illustrative embodiments of FIGS. 11A-11E is shown in reference to a posterior approach, but lateral SI joint stabilizing approaches with similar configurations may also be utilized. Referring to FIG. 11A, in one embodiment, the size, position, shape, and orientation of a defect may be planned by utilizing simulated defect images (98) overlaid upon preoperative or intraoperative images of the subject SI joint (6) anatomy. Referring to FIG. 11B, a generally oval defect (100) may be created from a posterior approach using tools such as one or more drills, osteotomes (such as those described in reference to FIGS. 7A-10B), or other orthopedic bone intervention tools. Referring to FIG. 11C, a bi-lobed defect (102) comprising two lobes (103, 104) connected by a midportion (105). A prosthesis occupying such geometry from a posterior approach provides several inherent stability qualities. For example, the lobes (103, 104) may be utilized relative to the cortical bone (8) positioning to interlock the sacral bone portion (2) relative to the ilium bone portion (4) and prevent relative motion of the prosthesis or bones. Further, the relatively large surface area may be an advantage for biological fixation (i.e., of bone tissue to porous material which preferably comprises the outer surface of a suitable prosthesis). FIG. 11D depicts a "H" shaped defect configuration (106) which may be occupied by an "H" shaped prosthesis comprising a central portion (112) and two end portions (108, 110). Such a configuration also provides desirable stability and fixation qualities. FIG. 11E depicts an "arcuate H" shaped defect (114) which may be occupied by an "arcuate H" shaped prosthesis. The defect and prosthesis may have a main body portion (116) and four or more arm portions (118), each of which may be generally arcuate shaped by virtue of a single joint-like bend (120), as in the embodiment of FIG. 11E, or a more gradual bend to define a smoothly arced arm (not shown). Other geometries may be utilized.

Referring to FIGS. 12A-15D, various generally hollow prosthesis configurations are depicted for press fit insertion into a defect which may be created using the aforementioned techniques. Their internal cavities may contain fixation catalysts at deployment time, as described above, and their walls generally comprise slots, holes, and other geometric features which are configured to enhance initial "scratch fit" fixation (i.e., when such prostheses are press fit into a defect with a hammer or other tool; in certain embodiments the prostheses may be configured to be under loads immediately when deployed, for interference/load bearing fit qualities; in other embodiments, the prosthesis geometry may be matched to the defect geometry without inherent stresses at deployment), as well as subsequent biological fixation. Generally, they may be machined or otherwise formed from materials such as nickel titanium surgical superalloy to mimic, at least to a relative degree, the mechanical properties of adjacent bony structural tissues.

Figure 12A:
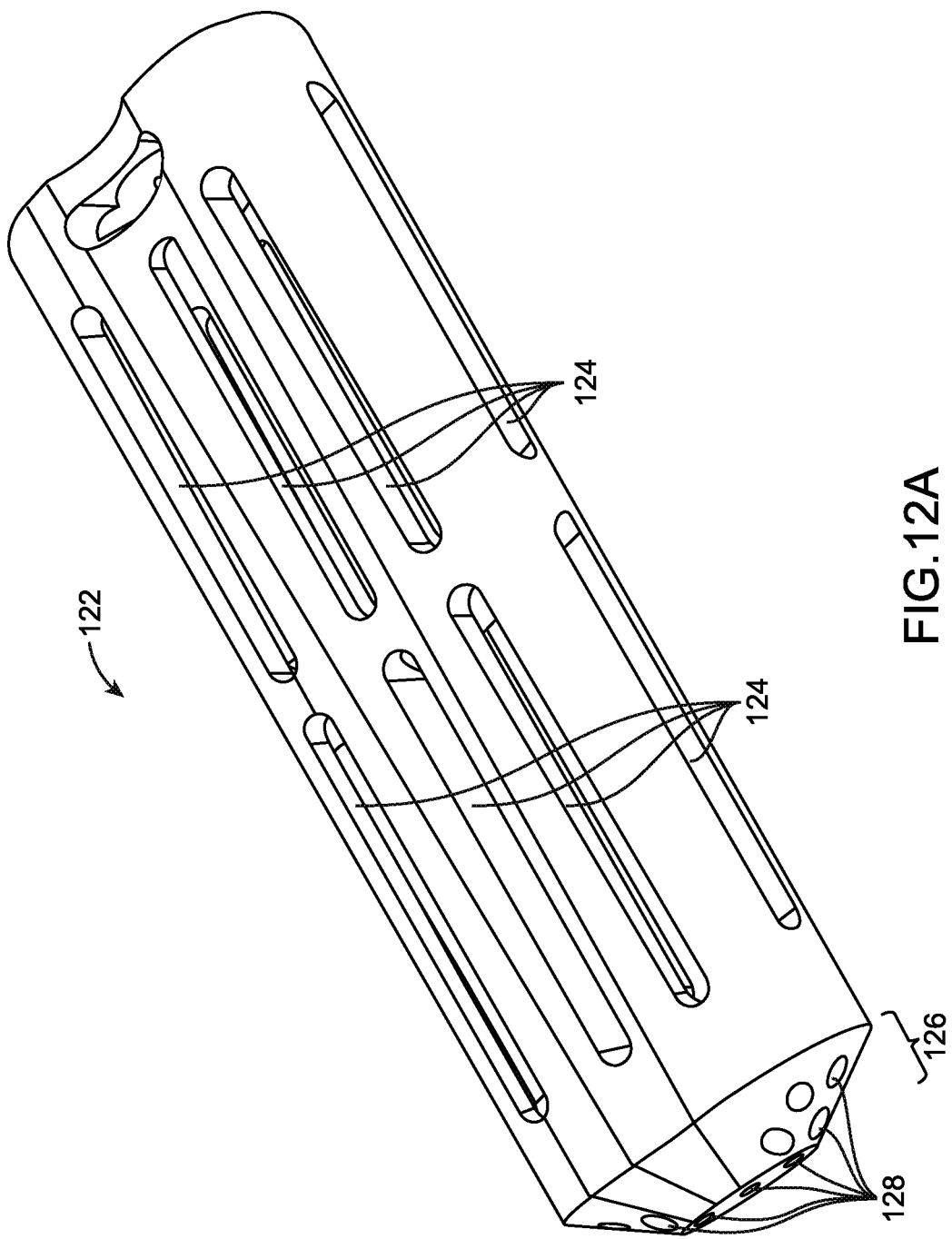
FIGS. 12A-12C illustrate one embodiment of a prosthesis suitable for stabilizing the sacro-iliac joint in accordance with the present invention.
Figure 12B:
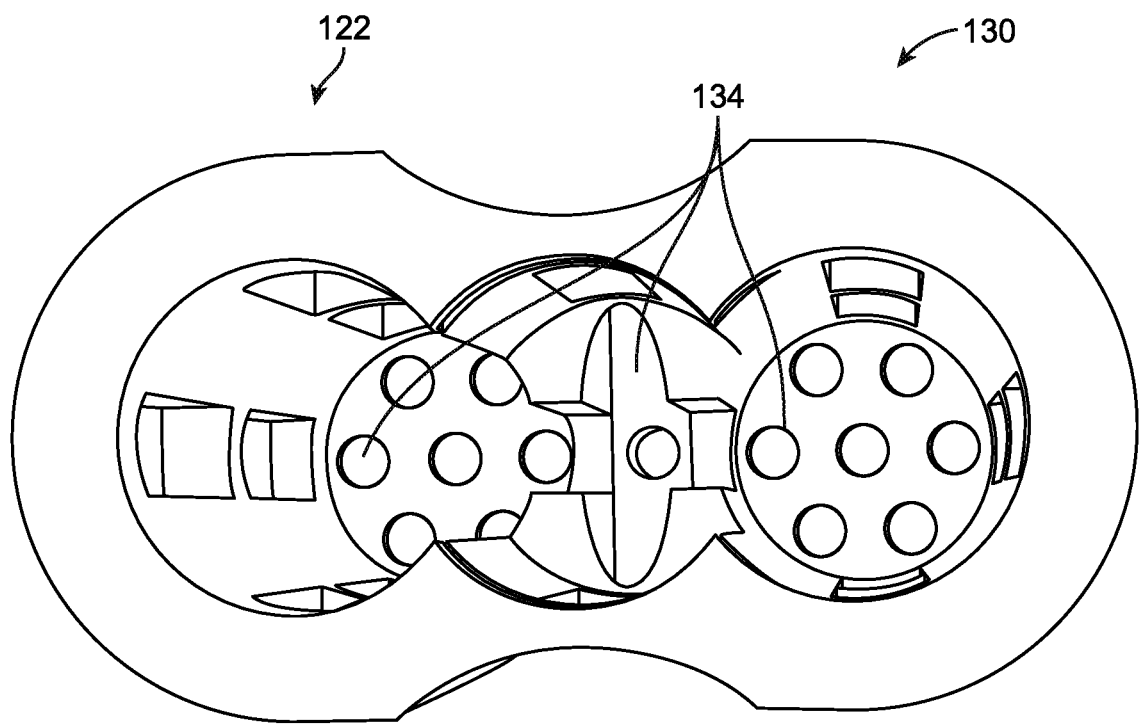
Figure 12C:
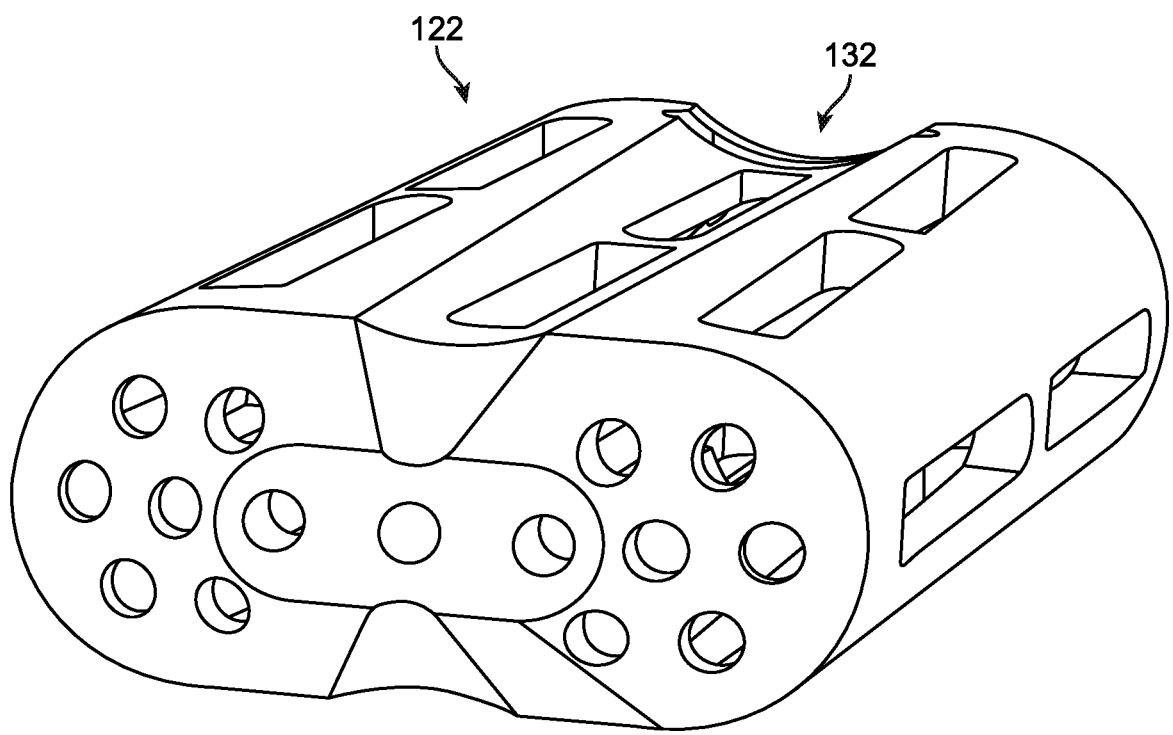

Referring to FIGS. 12A-12C, a single taper prosthesis embodiment (122) is depicted in various orthogonal views having a plurality of slots (124) and distal holes (128) configured to optimize structural performance and promote biological fixation. A tapered distal portion (126) is geometrically configured to assist with insertion upon deployment. An inverse taper (132) of the midportion (between the two outer lobes cross-sectionally) is defined longitudinally. A substantial interior volume (134) may be occupied by deployment tools and/or fixation catalysts, as described above.

Figure 13A:
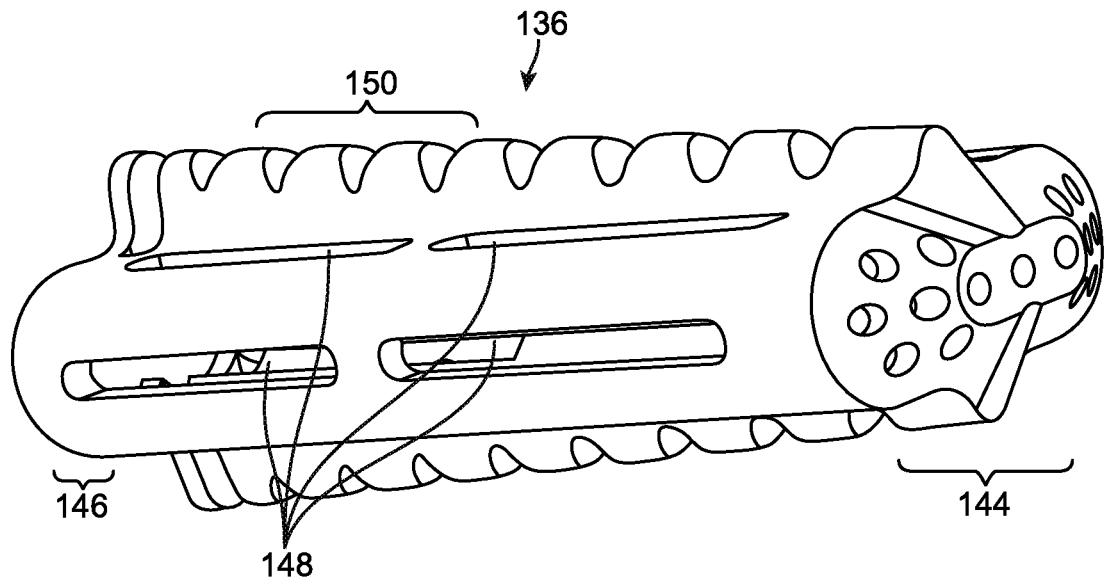
FIGS. 13A-13B illustrate one embodiment of a prosthesis suitable for stabilizing the sacro-iliac joint in accordance with the present invention.
Figure 13B:
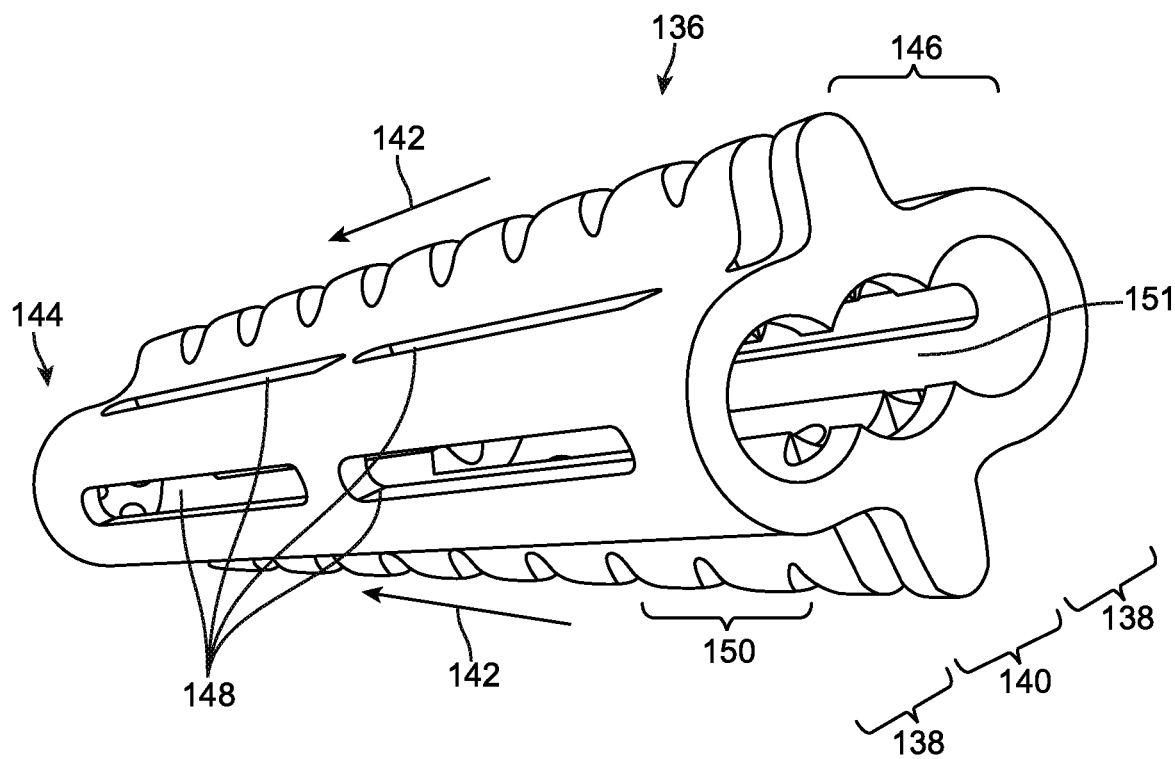

Referring to FIGS. 13A-13B, another single taper prosthesis embodiment (136) is depicted in two orthogonal views. The embodiment of FIGS. 13A-B is somewhat similar to that of FIGS. 12A-12C; one significant departure is a positive taper of the midportion (in between the end portions (138))—to define two ridges with interrupted ridge (150) features and a generally longitudinally tapering (142) ridge/midportion geometry that extends out farther proximally (146) than distally (144). A substantial interior volume (151) may be occupied by deployment tools and/or fixation catalysts, as described above.

Figure 14A:
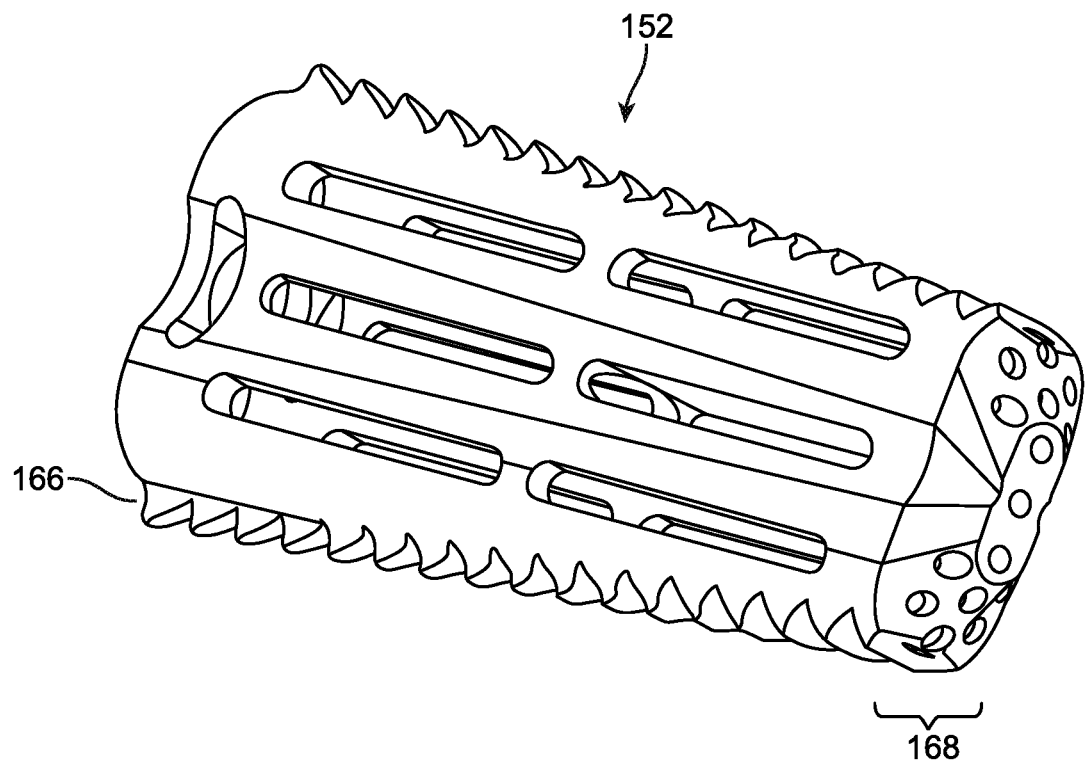
FIGS. 14A-14C illustrate one embodiment of a prosthesis suitable for stabilizing the sacro-iliac joint in accordance with the present invention.
Figure 14B:
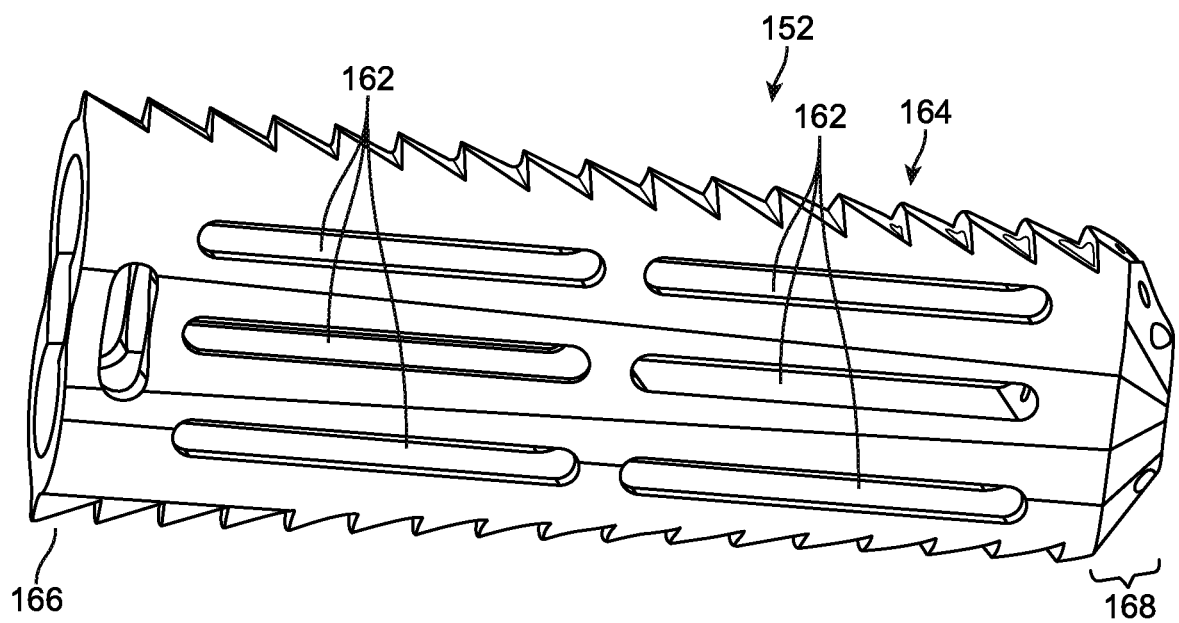
Figure 14C:
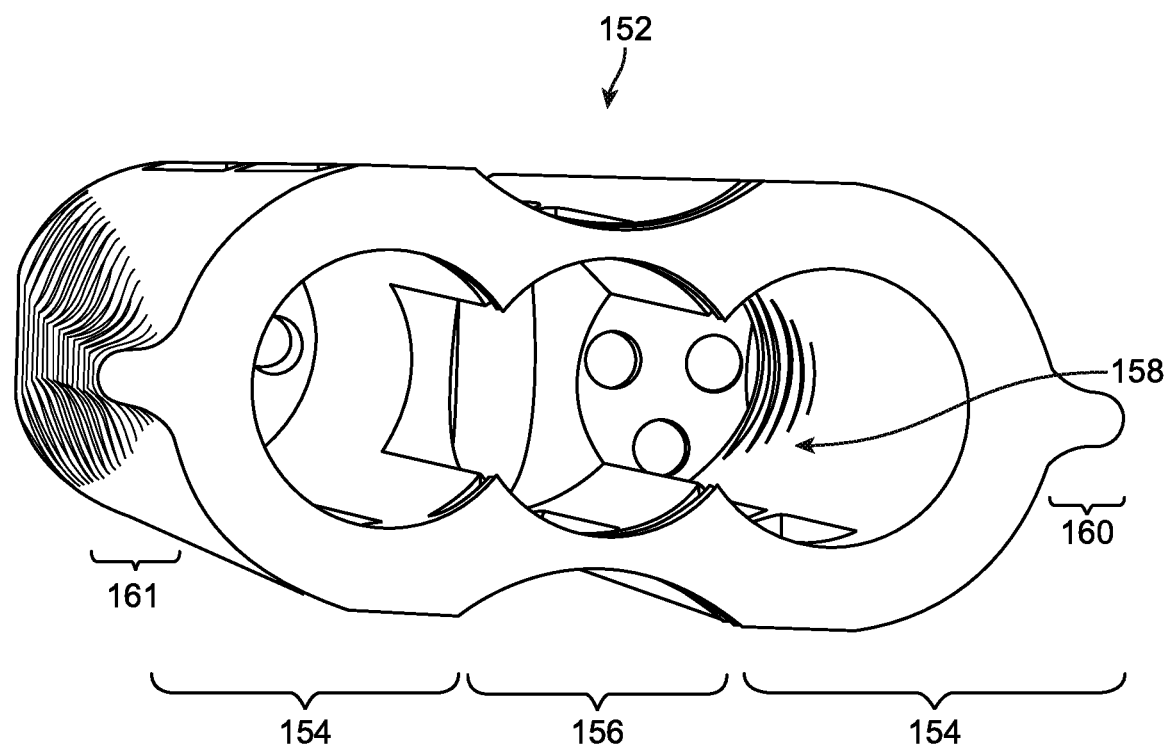
Figure 15A:
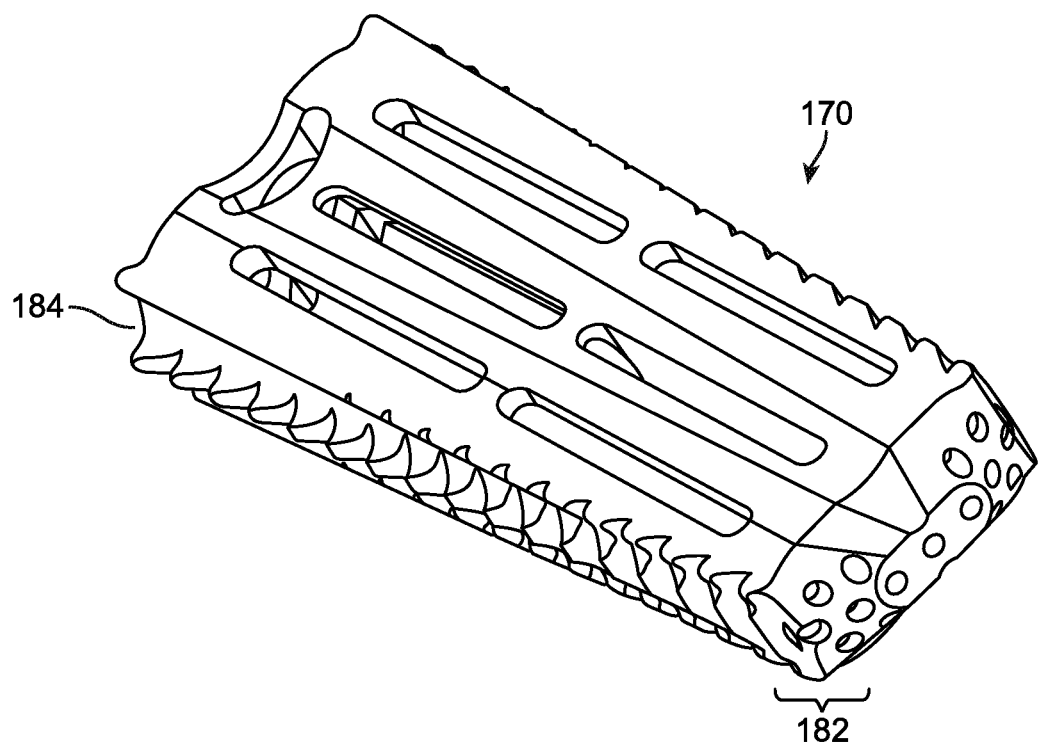
FIGS. 15A-15D illustrate one embodiment of a prosthesis suitable for stabilizing the sacro-iliac joint in accordance with the present invention.
Figure 15B:
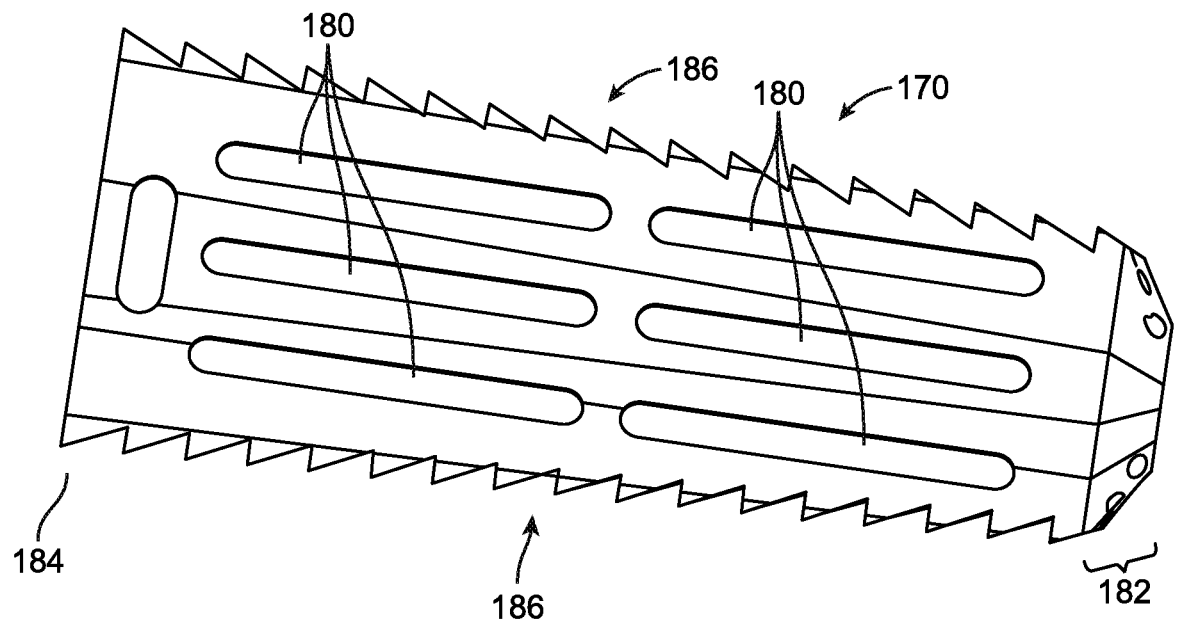
Figure 15C:
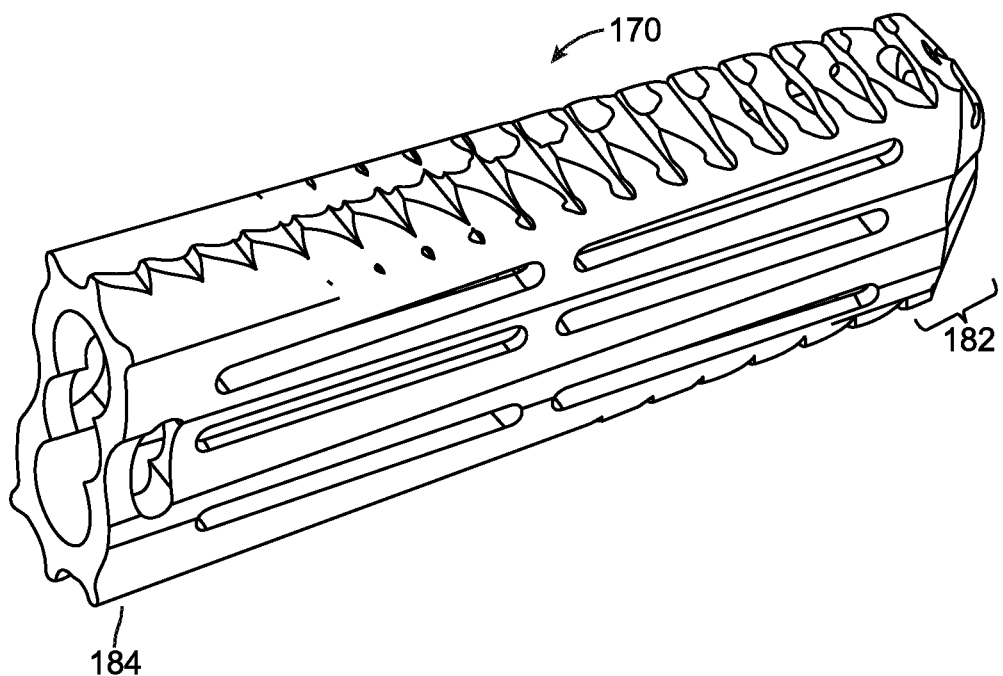
Figure 15D:
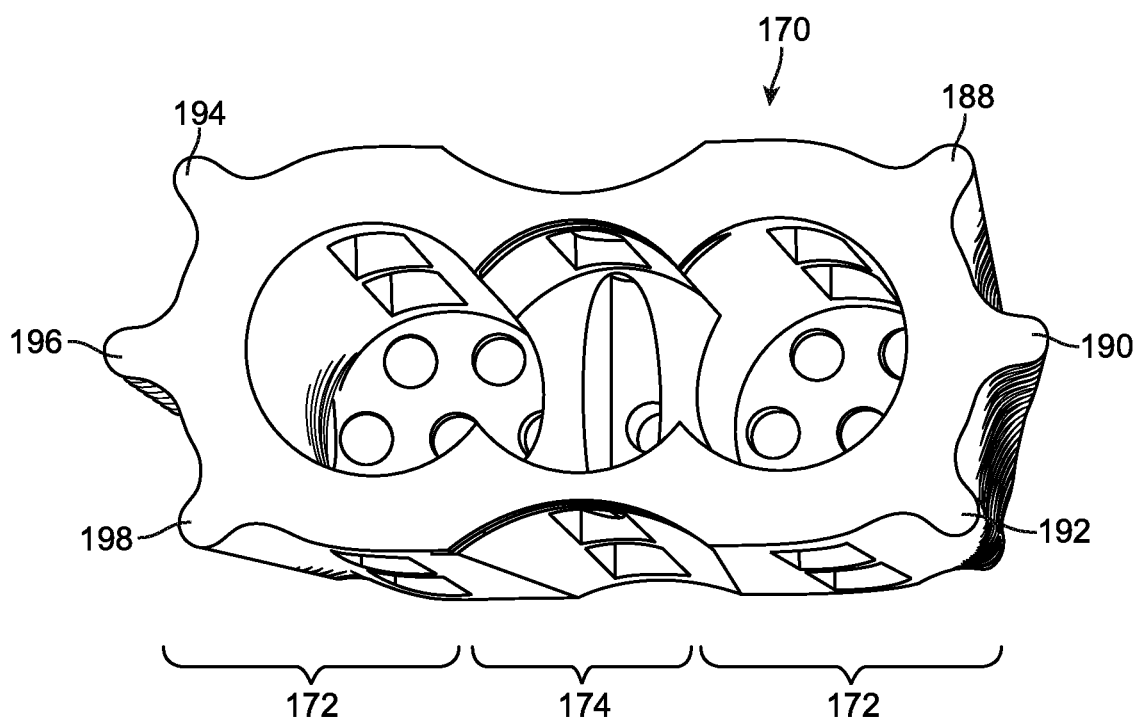

Referring to FIGS. 14A-14C, a dual taper prosthesis embodiment (152) is depicted in three orthogonal views. This embodiment also has a plurality of slots (162) and distal end (168) holes. The midportion (156) in between the two outer lobed portions (154) has an inverse taper providing a smaller cross sectional geometry proximally. The outer portions (154) each define an interrupted ridge (164) that defines two winglets (160, 161) and tapers in the inverse direction relative to the tapering of the midportion (156). An interior volume is easily accessed proximally (166).

FIGS. 15A-15D depict another dual taper prosthesis embodiment (170) having three winglet ridges (188, 190, 192/194, 196, 198) on each of two outer portions (172), and inverted tapering oriented longitudinally in relationship to the midportion (174) relative to the end portions (172).

Figure 16A:
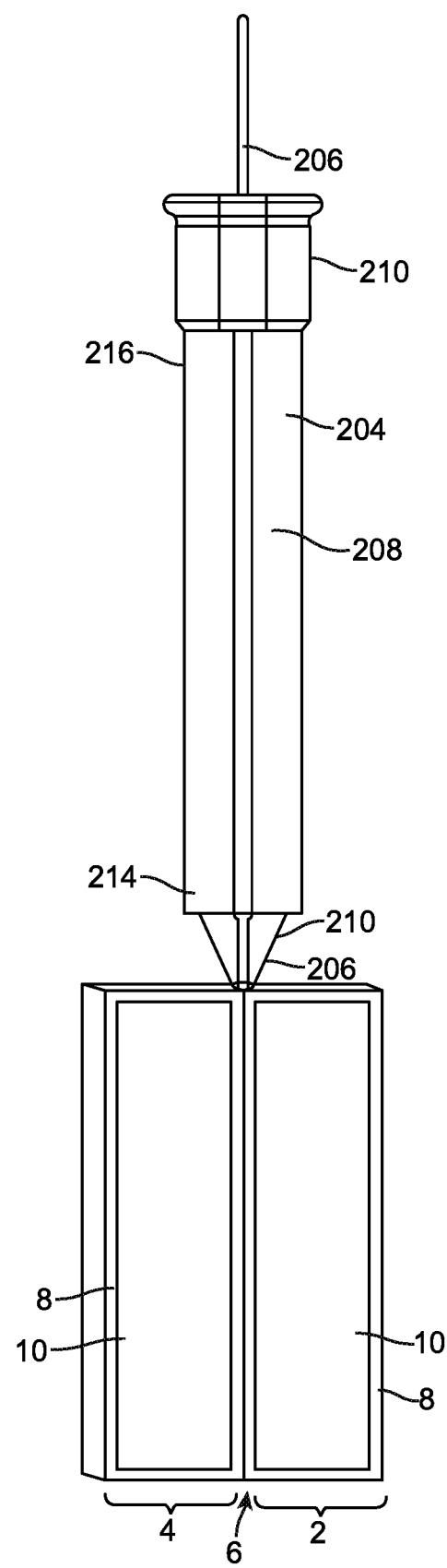
FIGS. 16A-16E illustrate embodiments of a prosthesis deployment system and method in accordance with the present invention.
Figure 16B:
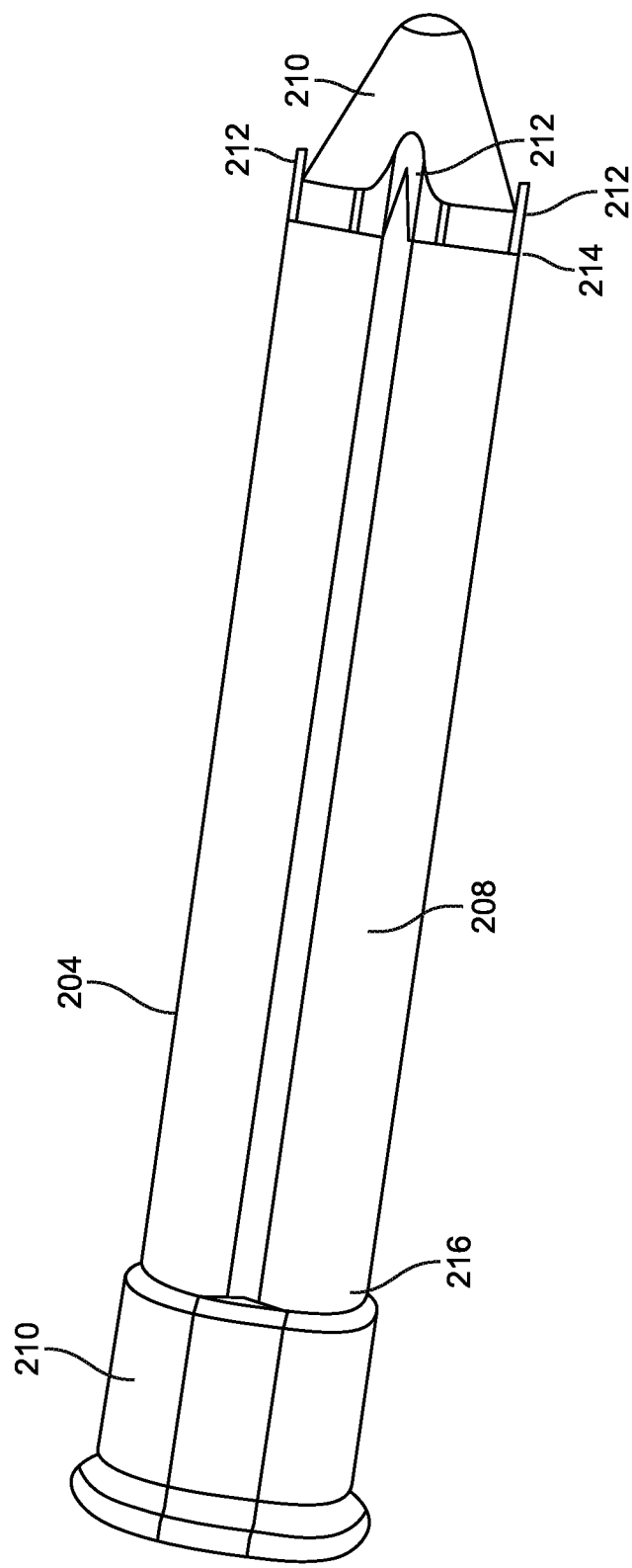
Figure 16C:
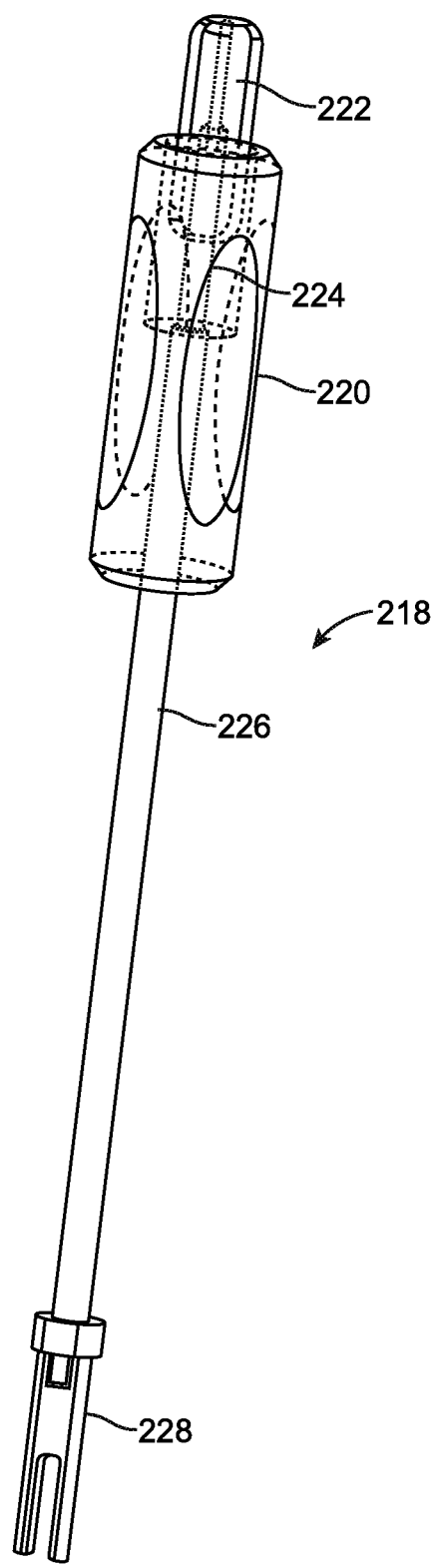
Figure 16D:
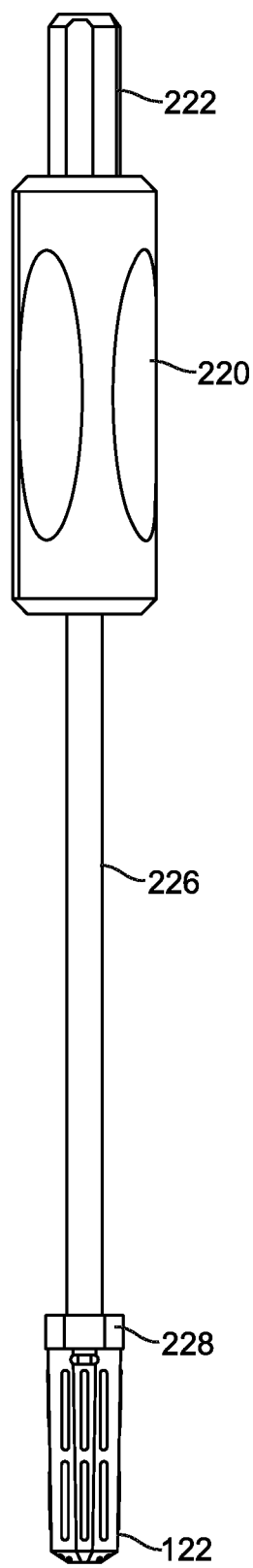
Figure 16E:
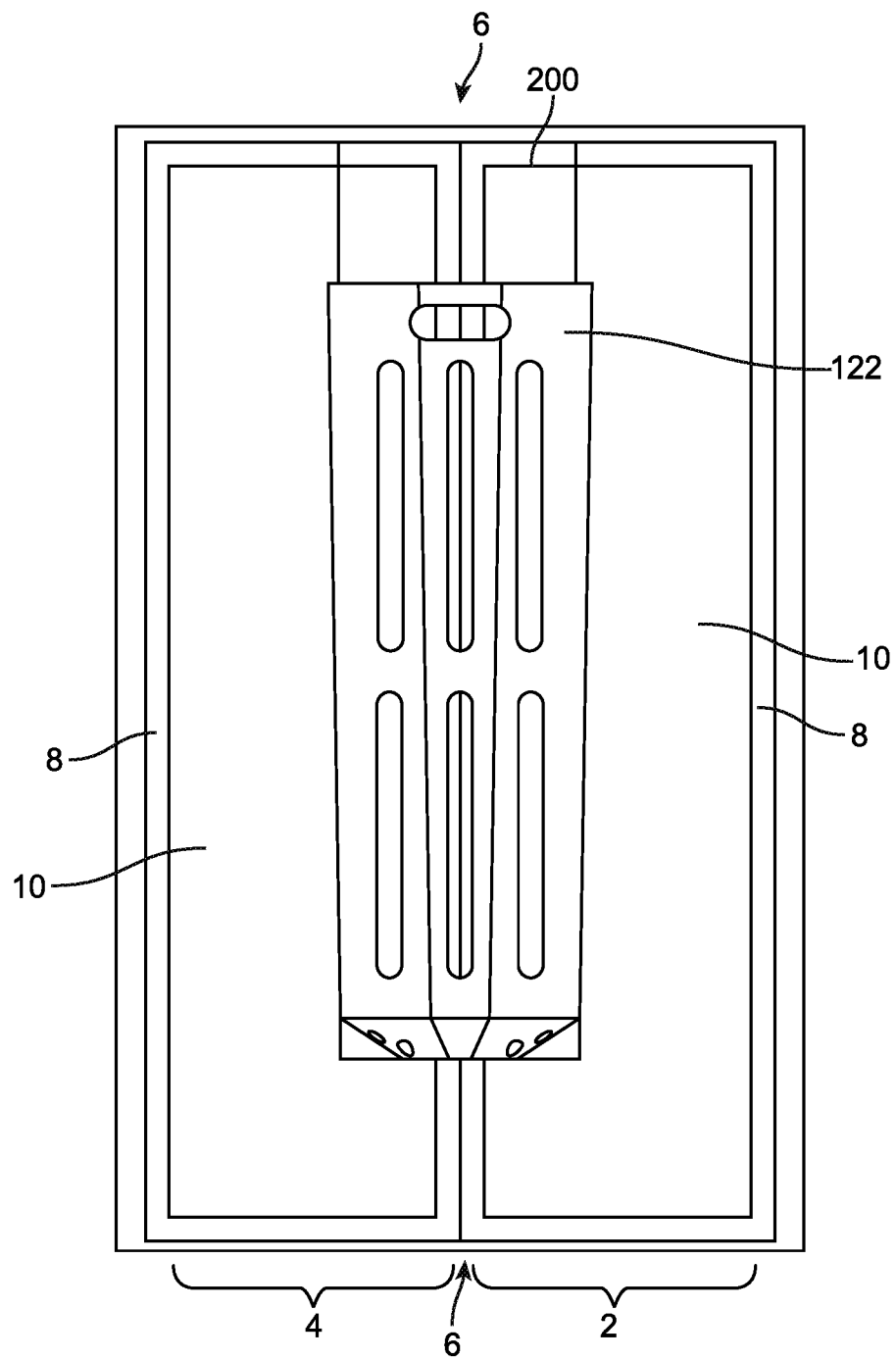

Referring to FIGS. 16A-16E, aspects of a deployment system and method utilizing configurations such as those described above in reference to FIGS. 1A-15D are illustrated. Referring to FIG. 16A, an osteotome/cannulation device (208) is temporarily coupled to an obturator (210). A guiding member (206), such as a guidewire or needle, has been partially advanced into an SI joint (6) and such advanced position confirmed using one or more imaging modalities as described above. A guiding member lumen or channel (208) may be utilized to guide the obturator/osteotome assembly (210/204) as they are advanced through portions of the bony structures (2, 4) defining the SI joint (6). The proximal end (216) of the osteotome (204) is fitted against an enlarged obturator portion which may be driven forward with a hammer or the like to advance the osteotome distal end (214). As shown in greater detail in FIG. 16B, the distal end of the osteotome (214) may comprise one or more teeth or apices (212) configured to assist with creation of a defect of one or more bony structure portions. After a defect of desired geometry and position has been created, such as by advancing the osteotome forward into the bony structures defining the SI joint (6), a prosthesis deployment assembly, such as that depicted in FIGS. 16C and 16D, may be utilized to advance a prosthesis, such as those depicted in FIGS. 12A-15D, into place within a defect (200). Two handles (220, 222) coupled to two shaft members (224, 226) may be utilized to advance and controllably deploy a prosthesis (122), such as the one shown coupled to the assembly in FIG. 16D, from a prosthesis interface (228), such as that depicted in FIGS. 16C and 16D. Referring to FIG. 16E, a deployed prosthesis (122) is depicted in situ providing stabilization and/or fixation to the SI joint (6) and bony structures (2, 4) defining it.

While multiple embodiments and variations of the many aspects of the invention have been disclosed and described herein, such disclosure is provided for purposes of illustration only. For example, wherein methods and steps described above indicate certain events occurring in certain order, those of ordinary skill in the art having the benefit of this disclosure would recognize that the ordering of certain steps may be modified and that such modifications are in accordance with the variations of this invention. Additionally, certain of the steps may be performed concurrently in a parallel process when possible, as well as performed sequentially. Accordingly, embodiments are intended to exemplify alternatives, modifications, and equivalents that may fall within the scope of the claims.

The invention claimed is:

1. A system for stabilizing a sacroiliac joint, comprising:
   a defect-creating tool assembly configured to be advanced from a posterior approach into a sacroiliac junction, said sacroiliac junction defined between sacrum and ilium structures of a patient,
   said defect-creating tool assembly comprising an elongated guide probe, a defect creation assembly, and prosthesis deployment assembly,
   said defect creation assembly adapted to create a first three-dimensional sacroiliac joint defect in said sacroiliac junction, said defect creation assembly comprising a first longitudinal axis, a defect creation assembly proximal end, a defect creation assembly distal end disposed opposite said defect creation assembly proximal end, and a guide member lumen that extends through said defect creation assembly, said guide member lumen adapted to receive said guide probe therein,
   said defect creation assembly further comprising a bone dislodging member disposed on said defect creation assembly distal end, said bone dislodging member adapted to dislodge portions of bone at said sacroiliac junction,
   said first three-dimensional sacroiliac joint defect comprising first and second lobe regions, said first lobe region being disposed in said sacrum and comprising a first sacrum defect shape, said second lobe region being disposed in said ilium and comprising a first ilium defect shape,
   said first three-dimensional sacroiliac joint defect comprising a first sacroiliac joint defect cross-sectional shape in a plane that intersects said sacrum and said ilium, said plane being substantially perpendicular to said first longitudinal axis of said defect creation assembly when said defect creation assembly is disposed in a defect creation position in said sacroiliac junction,
   said first sacroiliac joint defect cross-sectional shape comprising said first sacrum defect shape and said first ilium defect shape,
   said first sacroiliac joint defect cross-sectional shape further comprising a second longitudinal axis in said plane and a first sacroiliac joint defect length along said second longitudinal axis,
   said prosthesis deployment assembly comprising an elongated guide member, said elongated guide member comprising a guide member proximal end and a guide member distal end disposed opposite said guide member proximal end,
   said elongated guide member further comprising a prosthesis engagement member operatively connected to said guide member distal end, said prosthesis engagement member comprising a prosthesis engagement member proximal end and a prosthesis engagement member distal end disposed opposite said prosthesis engagement member proximal end,
   said prosthesis engagement member further comprising first and second elongated prosthesis guide rods extending from said prosthesis engagement member distal end; and
   a prosthesis comprising an integral member comprising first and second elongated partially cylindrical sections connected to a bridge section, whereby said prosthesis comprises a continuous exterior surface comprising first and second partially cylindrical surface regions, said first partially cylindrical surface region comprising a first partially cylindrical surface region shape that corresponds to at least a first portion of said sacrum defect shape, said second partially cylindrical surface region comprising a second partially cylindrical surface region shape that corresponds to at least a first portion of said ilium defect shape,
   said bridge section comprising a bridge section proximal end and a bridge section distal end disposed opposite said bridge section proximal end, said bridge section distal end comprising a first tapered region,
   at least said first and second elongated partially cylindrical sections solely comprising metal structures,
   said first elongated partially cylindrical section of said prosthesis comprising a first internal prosthesis engagement member lumen extending from said prosthesis proximal end, said first internal prosthesis engagement member lumen adapted to receive said first elongated prosthesis guide rod of said prosthesis engagement member,
   said second elongated partially cylindrical section of said prosthesis comprising a second internal prosthesis engagement member lumen extending from said prosthesis proximal end, said second internal prosthesis engagement member lumen adapted to receive said second elongated prosthesis guide rod of said prosthesis engagement member,
   said prosthesis further comprising a first plurality of slots, a second plurality of said first plurality of slots being in communication with said first internal prosthesis engagement member lumen and a third plurality of said first plurality of slots being in communication with said second internal prosthesis engagement member lumen,
   said continuous exterior surface of said prosthesis further defining a prosthesis cross-sectional shape comprising a third longitudinal axis, said prosthesis cross-sectional shape comprising a prosthesis cross-sectional shape length along said third longitudinal axis,
   said prosthesis cross-sectional shape length being greater than said first sacroiliac joint defect length at at least a first region of said first three-dimensional sacroiliac joint defect,
   said prosthesis being sized and adapted to be inserted into said first three-dimensional sacroiliac junction defect, wherein said second longitudinal axis of said first sacroiliac joint defect is substantially coincident with said third longitudinal axis of said prosthesis, and said prosthesis is press-fit in said first three-dimensional sacroiliac junction defect and induces a transition of said first three-dimensional sacroiliac junction defect to a second three-dimensional sacroiliac junction defect, said second three-dimensional sacroiliac junction defect comprising a second three-dimensional sacroiliac junction defect shape comprising a fourth longitudinal axis, at least a first region of said second three-dimensional sacroiliac junction defect shape comprising a second sacroiliac joint defect length along said fourth longitudinal axis, said second sacroiliac joint defect length corresponding to said prosthesis cross-sectional shape length.

2. The system of claim 1, wherein said first elongated partially cylindrical section of said prosthesis comprises a third proximal end and a third distal end disposed opposite said third proximal end and said first proximal end of said prosthesis and said second elongated partially cylindrical section comprises a fourth proximal end and a fourth distal end disposed opposite said fourth proximal end and said first proximal end of said prosthesis.

3. The system of claim 2, wherein said third distal end of said first elongated partially cylindrical section comprises a second tapered region and said fourth distal end of said second elongated partially cylindrical section comprises a third tapered region.

4. The system of claim 1, further comprising an image capture device configured to intraoperatively capture images of said defect-creating tool assembly relative to portions of said sacrum and ilium.

5. The system of claim 4, wherein said image capture device is selected from the group consisting of a fluoroscope, a CT system, an ultrasound system, a radiography system, and a magnetic resonance imaging system.

6. The system of claim 1, wherein said prosthesis further comprises a fixation catalyst selected from the group consisting of demineralized bone matrix, autograft bone material, allograft bone material, polymethylmethacrylate, and a bone morphogenic protein.

7. The system of claim 6, wherein said bone morphogenic protein is selected from the group consisting of BMP-1, BMP-7, and OP-1.

* * * * *